United States Patent
Shibuya et al.

(10) Patent No.: US 11,059,888 B2
(45) Date of Patent: Jul. 13, 2021

(54) REGULATORY T CELL ACTIVATOR AND USE THEREOF

(71) Applicant: University of Tsukuba, Tsukuba (JP)

(72) Inventors: Akira Shibuya, Tsukuba (JP); Kazuko Shibuya, Tsukuba (JP); Fumie Abe, Tsukuba (JP); Rei Hirochika, Tsukuba (JP); Genki Okumura, Tsukuba (JP)

(73) Assignee: University of Tsukuba, Tsukuba (JP)

( * ) Notice: Subject to any disclaimer, the term of this patent is extended or adjusted under 35 U.S.C. 154(b) by 20 days.

(21) Appl. No.: 16/095,024

(22) PCT Filed: Apr. 19, 2017

(86) PCT No.: PCT/JP2017/015767
§ 371 (c)(1),
(2) Date: Oct. 19, 2018

(87) PCT Pub. No.: WO2017/183665
PCT Pub. Date: Oct. 26, 2017

(65) Prior Publication Data
US 2019/0127462 A1    May 2, 2019

(30) Foreign Application Priority Data

Apr. 20, 2016   (JP) ............................ JP2016-084170

(51) Int. Cl.
| | | |
|---|---|---|
| *C07K 16/28* | (2006.01) | |
| *C12N 15/09* | (2006.01) | |
| *C12N 5/10* | (2006.01) | |
| *A61K 39/395* | (2006.01) | |
| *A61P 1/16* | (2006.01) | |
| *A61P 37/06* | (2006.01) | |
| *A61P 13/12* | (2006.01) | |
| *A61P 1/00* | (2006.01) | |
| *A61K 39/00* | (2006.01) | |

(52) U.S. Cl.
CPC ........ *C07K 16/2803* (2013.01); *A61K 39/395* (2013.01); *A61P 1/00* (2018.01); *A61P 1/16* (2018.01); *A61P 13/12* (2018.01); *A61P 37/06* (2018.01); *C07K 16/28* (2013.01); *C12N 5/10* (2013.01); *C12N 15/09* (2013.01); *A61K 2039/505* (2013.01); *C07K 2317/21* (2013.01); *C07K 2317/56* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| | | |
|---|---|---|
| 8,822,642 B2 | 9/2014 | Levin et al. |
| 9,873,740 B2 | 1/2018 | Grogan et al. |
| 2009/0186017 A1 | 7/2009 | Shibuya et al. |
| 2011/0318762 A1 | 12/2011 | Shibuya et al. |
| 2013/0095102 A1 | 4/2013 | Levin et al. |
| 2015/0216970 A1 | 8/2015 | Grogan et al. |
| 2017/0037127 A1 | 2/2017 | Grogan et al. |
| 2017/0044256 A1 | 2/2017 | Grogan et al. |

FOREIGN PATENT DOCUMENTS

| | | |
|---|---|---|
| EA | 022932 B1 | 3/2016 |
| JP | 5296530 B2 | 6/2013 |
| JP | 2013193995 A | 9/2013 |
| JP | 2013245162 A | 12/2013 |
| WO | 2015/009856 A2 | 1/2015 |

OTHER PUBLICATIONS

Tomasec et al., 2005, Nature Immunology, vol. 6: 181-188 Progress in Autoimmune Disease Research, 2005, pp. 1-126.*
Moore et al., 2016: Am. J. Path. vol. 186: 1978-1981 MS the disease, National Multiple Sclerosis Society, pp. 1-3.*
Dondelinger et al., 2018, Front. Immunol. vol. 9: 1-15 Quinn et al., 2001, Best Pract. Res. Clin. Rheum. vol. 15: 49-66.*
Chevalier, 2013, Blood, vol. 121: 29-37 Scott et al., 2012, Nature Rev. vol. 12: 278-287.*
Fang, L. et al., "Expression of CD226 Antagonizes Apoptotic Cell Death in Murine Thymocytes", J Immunol, 182 (9): 5453-5460.
Hou, S. et al., "CD226 Protein Is Involved in Immune Synapse Formation and Triggers Natural Killer (NK) Cell Activation via Its First Extracellular Domain", The Journal of Biological Chemistry, 289 (10): pp. 6969-6977.
Rudikoff et al., "Single amino acid substitution of altering antigenbinding specificity", Proceedings of the National Academy of Sciences of the United States of America, Immunology, Mar. 1982, pp. 1979-1983, vol. 79, No. 6.
Diamond et al., "Somatic mutation of the T15 heavy chain gives rise to an antibody with autoantibody specificity", Proceedings of the National Academy of Sciences of the United States of America, Immunology, Sep. 1984, pp. 5841-5844, vol. 81, No. 18.
Ohno et al., "Antigen-binding specificities of antibodies are primarily determined by seven residues of VH", Proceedings of the National Academy of Sciences of the United States of America, Immunology, May 1985, pp. 2945-2949, vol. 82, No. 9.
Pakula et al., "Genetic analysis of protein stability and function", Annu. Rev. Genet., 1989, pp. 289-310, vol. 23, Annual Reviews Inc.
Frankel et al., "Characterization of diphtheria fusion proteins targeted to the human interleukin-3 receptor", Protein Engineering, Design and Selections, 2000, pp. 575-581, vol. 13, No. 8, Oxford University Press.
Yarilin A. A., Fundamentals of Immunology: A Textbook, 1999, pp. 172-174, Medistina.
Jia W. et al., "Preparation and Characterization of MAbs Against Different Epitopes of CD226 (PTA1)", Hybridoma, 2000, pp. 489-494, vol. 19, No. 6.
Martin A. C. R., "Protein sequence and structure analysis of antibody variable domains", Antibody Engineering, 2010, pp. 44-45, vol. 2.

(Continued)

Primary Examiner — Amy E Juedes
(74) Attorney, Agent, or Firm — The Webb Law Firm

(57) ABSTRACT

A regulatory T cell activator including a substance that inhibits the binding between DNAX accessory molecule-1 (DNAM-1) and CD155.

2 Claims, 23 Drawing Sheets

Specification includes a Sequence Listing.

(56) References Cited

OTHER PUBLICATIONS

Finkelstein A. V. et al., Protein Physics: Lecture course with color and stereoscopic illustrations and tasks: a training manual, 4th edition, 2012, pp. 23.

Nabekura T. et al., "Costimulatory Molecule DNAM-1 Is Essential for Optimal Differentiation of Memory Natural Killer Cells during Mouse Cytomegalovirus Infection", Immunity, 2014, pp. 225-234, vol. 40.

Shibuya, A, et al., DNAM-1, A Novel Adhesion Molecule Involved in the Cytolytic Function of T Lymphocytes, Immunity, Jun. 1996, pp. 573-581, vol. 4,Cell Press.

Tahara-Hanaoka, S, et al., Identification and characterization of murine DNAM-1 (CD226) and its poliovirus receptor family ligands, Biochemical and Biophysical Research Communications, 2005, pp. 996-1000, vol. 329, Elsevier, Inc.

Koyama, Motoko, et al., Promoting regulation via inhibition of DNAM-1 after transplantation, Blood, 2013, pp. 3511-3520, vol. 121, No. 17, The American Society of Hematology.

Shibuya, Akira, DNAM-1(CD226) ni yoru Killer Rinpakyu Kasseika to Hyoteki Saibo Shogai, Infection, Inflammation, and Immunity, 2013, pp. 24-34, vol. 43.

Yamashita, Yumi, et al., Establishment and Characterization of a Novel Anti-DNAM-1 Monoclonal Antibody, Monoclonal Antibodies in Immunodiagnosis and Immunotherapy, 2013, pp. 60-64, vol. 32, No. 1, Mary Ann Liebert, Inc.

Dardalhon et al., "CD226 Is Specifically Expressed on the Surface of Th1 Cells and Regulates Their Expansion and Effector Functions", The Journal of Immunology, vol. 175, No. 3, Aug. 2005, pp. 1558-1565.

Gilfillan et al., "DNAM-1 Promotes Activation of Cytotoxic Lymphocytes by Nonprofessional Antigen-Presenting Cells and Tumors", The Journal of Experimental Medicine, vol. 205, No. 13, Dec. 2008, pp. 2965-2973.

Nabekura et al., "Critical Role of DNAX Accessory Molecule-1 (DNAM-1) in the Development of Acute Graft-Versus-Host Disease in Mice", Proceedings of the National Academy of Sciences, vol. 107, No. 43, Oct. 2010, pp. 18593-18598.

Lozano et al., "The CD226/CD155 Interaction Regulates the Proinflammatory (Th1/Th17)/Anti-Inflammatory (Th2) Balance in Humans", The Journal of Immunology, vol. 191, No. 7, Oct. 2013, pp. 3673-3680.

* cited by examiner

Fig. 1

```
No.1   1   -SQSLSLTCSVTGYSITSGYYWNWIRQFPGNKLEWMGYISYDGSNNYNPS  50
No.2   1   -SQSLSLTCTVTGYSITSDYAWNWIRQFPGNKLEWMGYISYSGTTTYNPS  50
No.3   1   ------EISCKASGYTFTNYWLGWVKQRPGHGLEWIGDIYPGGGYTNYNE  50
No.4   1   -KWGLSEISCKASGYTFTDYNMHWVKQSHGKSLEWIGYIYPYNGGTGYNQ  50
No.5   1   ---------SVTGYSITSG-YYWNWIRQFPGNKLEWMGYISYDGSNNYNPS 50
No.6   1   SQSLSLTCSVTGYSITSG-YYWNWIRQFPGNKLEWMGYISYDGSNNYNPS  50
                      CDR1                    CDR2

No.1  51   LKNRISITRDTSKNQFFLKLNSVTTEDTATYYCARAYYGNYVGYFDVWGA  100
No.2  51   LKSRISITRDTSKNQFFLQLNSVTTEDTATYYCAELSMDYWGQGTSVTVS  100
No.3  51   KFKGKATLTADTSSSTAYMQLSSLTSEDSAVYFCANAYYRYKGFAYWGQG  100
No.4  51   KFKSKATLTVDNSSSTAYMELRSLTSEDSAVYYCAGYWYFDVWGAGTTVT  100
No.5  51   LKNRISITRDTSKNQFFLKLNSVTTEDTATYYCARERVMITASFDYWGQG  100
No.6  51   LKNRISITRDTSKNQFFLKLNSVTTEDTATYYCARERVMITASFDYWGQG  100
                                           CDR3

No.1 101   GTTVTVSSAKTTPPSVYPLAPGK------------------------  122
No.2 101   SAKTTPPSVYPLAPGNLSSTSFSSLG--------------------  126
No.3 101   TLVTVSAAKTTAPSVYPLAPL-------------------------  115
No.4 101   VSSAKTTPPSVYPLAPWK----------------------------  117
No.5 101   TTLTVSSAKTTPPSVYPLAPGK------------------------  113
No.6 101   TTLTVSSAKTTPPSVYPLAPGK------------------------  121
```

Fig. 2

```
No.1    1   ------------------RVTITCKASQSVSNDVAWYQQKPGQSPKLLIYY   50
No.2    1   DIVLSQSPAILSVSPGERVSFSCRASQSIGTSIHWYQQRTNGSPRLLIKY   50
No.3    1   ---------------VTMSCKSSQSLLYSSNQKNYLAWYQQKPGQAPKLLIYW   50
No.4    1   ------------------EKVSITCKASQDVGTAVAWYQQKPGQSPKLLIYW   50
No.5    1   -------------SALWERVSLTCRASQEISGYLSWLQQKPDGTIKRLIYA   50
No.6    1   --------------------------RASGNIHNYLAWYQQKQGKSPQLLVYN   50
                                        CDR1

No.1   51   ASNRYTGVPDRFTGSGYGTDFTFTISTVQAEDLAVYFCQQDYSSPLTFGA  100
No.2   51   ASESISGIPSRFSGSGSGTDFTLSINSVESEDIADYYCQQSRSWPLTFGA  100
No.3   51   ASTRESGVPDRFTGSGSGTDFTLTISSVKAEDLAVYYCQQYYSYPWTFGG  100
No.4   51   ASTRHTGVPDRFTGSGSGTDFTLTISNVQSEDLADYFCQQYSSYPWTFGG  100
No.5   51   ASTLDSGVPKRFSGSRSGSDYSLTISSLESEDFADYYCLQYASYPWTFGG  100
No.6   51   AKTLADGVPSRFSGSGSGTQYSLKINSLQPEDFGSYYCQHFWSTPYTFGG  100
              CDR2                                    CDR3

No.1  101   GTKLELKRADAAPTVSIFPPSSEQT-------------------------  108
No.2  101   GTKLELKRADAAPTVSIFPPSSEQNHEFWIRYVTRLQHAWYRAFPIGVDE  150
No.3  101   GTKLEIKRADAAPTVSIFPPSSEQ----------------------------  112
No.4  101   GTKLEIKRADAAPTVSIFPPSSEQR----------------------------  109
No.5  101   GTKLEIKRADAAPTVSIFPPSSEQ----------------------------  112
No.6  101   GTKLEIKRADAAPTVSIFPP-----------------------------   97
```

(a)

(b)

(a)

(b)

(a)

WT (b)

DNAM-1 KO (c)

(a)

(b)

(c)

REGULATORY T CELL ACTIVATOR AND USE THEREOF

CROSS-REFERENCE TO RELATED APPLICATIONS

This application is the United States national phase of International Application No. PCT/JP2017/015767 filed Apr. 19, 2017, and claims priority to Japanese Patent Application No. 2016-084170 filed Apr. 20, 2016, the disclosures of which are hereby incorporated in their entirety by reference.

The Sequence Listing associated with this application is filed in electronic format via EFS-Web and is hereby incorporated by reference into the specification in its entirety. The name of the text file containing the Sequence Listing is 1806767_ST25.txt. The size of the text file is 16,684 bytes, and the text file was created on Oct. 19, 2018.

TECHNICAL FIELD

The present invention relates to a regulatory T cell activator and the use of the regulatory T cell activator. Specifically, it relates to a regulatory T cell activator, a pharmaceutical composition for activation of regulatory T cells, an anti-human DNAX Accessory Molecule-1 (DNAM-1) monoclonal antibody or a fragment thereof, nucleic acid, a vector, and a transformant. The present application is based upon and claims the benefit of priority of the prior Japanese Patent Application No. 2016-084170, filed on Apr. 20, 2016, which is hereby incorporated by reference herein in its entirety.

BACKGROUND ART

Graft-versus-host disease (GVHD) may occur after blood transfusion or a stem cell transplant. Graft-versus-host disease is caused by active T cells of donor origin which are present in the transplanted cells damaging the cells of the recipient. Rejection may occur when an organ of a donor is transplanted into a recipient. For example, in a heart transplant, a vascular transplant, kidney transplant and the like, a transplanted heart, vessel, or kidney temporarily engrafts but may gradually become detached. Accordingly, there has been a demand for a technology for preventing graft-versus-host disease and transplant rejection.

For example, in Japanese pattent document JPA 2013-245162, it is described that a neutralizing antibody to mouse DNAM-1 protein can be used as a drug for maintaining the engraftment of a transplanted heart, vessel, or kidney in mice.

DNAM-1 protein, also known as CD226, is an adhesion molecule having a molecular weight of 65 kDa which belongs to the immunoglobulin superfamily. DNAM-1 protein is expressed on various human and mouse immunocytes, such as $CD4^+$ t cells, CD8+ cells, NK cells, macrophages, and dendritic cells. The RefSeq ID of human DNAM-1 is NP_001290547. The RefSeq ID of mouse DNAM-1 is NP_001034238. The inventors found that DNAM-1 protein binds to CD155, which has been known as a poliovirus receptor. CD155 is a type I transmembrane glycoprotein that belongs to the immunoglobulin superfamily.

PTL 1: JPA 2013-245162

SUMMARY OF INVENTION

Technical Problem

In light of the above context, it is an object of the present invention to provide a technology for reducing human immune responses.

Solution to Problem

The present invention includes the following aspects.

[1] A regulatory T cell activator comprising a substance that inhibits binding between DNAM-1 and CD155.

[2] The regulatory T cell activator according to [1], wherein the substance that inhibits binding between DNAM-1 and CD155 is a substance that specifically binds to DNAM-1, an agent that inhibits expression of DNAM-1, a substance that specifically binds to CD155, or an agent that inhibits expression of CD155.

[3] The regulatory T cell activator according to [1] or [2], used for preventing or treating graft-versus-host disease, transplant rejection, an autoimmune disease, fibrosis, inflammatory enteritis, or an allergy.

[4] The regulatory T cell activator according to any one of [1] to [3], wherein the substance that inhibits binding between DNAM-1 and CD155 is a substance that specifically binds to DNAM-1, wherein the DNAM-1 is human DNAM-1, wherein the substance that specifically binds to DNAM-1 is an antibody or fragment thereof, and wherein the antibody or fragment thereof is capable of saturating human DNAM-1 forcibly expressed on surfaces of $1\times10^5$ lymphocytes when reacted with the human DNAM-1, the amount of the antibody or fragment thereof being 100 ng or less in terms of the full-length of IgG type antibody.

[5] The regulatory T cell activator according to any one of [1] to [4], wherein the substance that inhibits binding between DNAM-1 and CD155 is a substance that specifically binds to DNAM-1, wherein the DNAM-1 is human DNAM-1, wherein the substance that specifically binds to DNAM-1 is an antibody or a fragment thereof, and wherein when the antibody or a fragment thereof is reacted after human DNAM-1 which is forcibly expressed on the surfaces of $1\times10^5$ lymphocytes is saturated by 1000 ng of a fusion protein which is formed by the fusion of human CD155 with an IgG antibody constant region, the antibody or a fragment thereof is capable of completely inhibiting binding between the fusion protein and human DNAM-1 with 500 ng or less in terms of full-length of IgG type antibody.

[6] The regulatory T cell activator according to [4] or [5], wherein the antibody is a human type antibody.

[7] The regulatory T cell activator according to any one of [4] to [6], wherein the antibody or a fragment thereof includes a heavy-chain variable region comprising complementarity determining regions (CDRs) 1 to 3 having amino acid sequences of SEQ ID NOs: 1 to 3, respectively, or amino acid sequences of SEQ ID NOs: 1 to 3, respectively, modified by deletion, substitution, or addition of one or several amino acids and a light-chain variable region comprising CDR1 to CDR3 having amino acid sequences of SEQ ID NOs: 4 to 6, respectively, or amino acid sequences of SEQ ID NOs: 4 to 6, respectively, modified by deletion, substitution, or addition of one or several amino acids, or competes with an antibody including a heavy-chain variable region comprising CDR1 to CDR3 having amino acid sequences of SEQ ID NOs: 1 to 3, respectively, and a light-chain variable region comprising CDR1 to CDR3 having amino acid sequences of SEQ ID NOs: 4 to 6 respectively when bound to human DNAM-1.

[8] The regulatory T cell activator according to any one of [4] to [7], wherein the antibody or the fragment thereof includes a heavy-chain variable region comprising CDR1 to CDR3 having amino acid sequences of SEQ ID NOs: 1 to 3 respectively, or amino acid sequences of SEQ ID NOs: 1 to 3 respectively modified by deletion, substitution, or addition of one or several amino acids, and a light-chain variable region comprising CDR1 to CDR3 having amino acid sequences of SEQ ID NOs: 4 to 6 respectively, or amino acid sequences of SEQ ID NOs: 4 to 6 respectively modified by deletion, substitution, or addition of one or several amino acids.

[9] A pharmaceutical composition for activation of regulatory T cells comprising the regulatory T cell activator according to any one of [1] to [8] and a pharmaceutically acceptable carrier.

[10] An anti-human DNAM-1 monoclonal antibody or the fragment thereof, being capable of saturating the human DNAM-1 forcibly expressed on surfaces of $1 \times 10^5$ lymphocytes with 100 ng or less in terms of the full-length of IgG antibody when the anti-human DNAM-1 monoclonal antibody or the fragment thereof is reacted with the human DNAM-1.

[11] An anti-human DNAM-1 monoclonal antibody or a fragment thereof, wherein when the human DNAM-1 forcibly expressed on the surfaces of $1 \times 10^5$ lymphocytes is reacted after the human DNAM-1 is saturated by 1000 ng of a fusion protein formed by human CD155 and an IgG antibody constant region, the anti-human DNAM-1 monoclonal antibody or a fragment thereof is capable of completely inhibiting binding between the fusion protein and the human DNAM-1 molecule with 500 ng or less in terms of the full-length IgG type antibody.

[12] The anti-human DNAM-1 monoclonal antibody or the fragment thereof according to [10] or [11], being a human type antibody or a fragment thereof.

[13] The anti-human DNAM-1 monoclonal antibody or the fragment thereof according to any one of [10] to [12], wherein the CDR1 to CDR3 have a heavy-chain variable region comprising amino acid sequences of SEQ ID NOs: 1 to 3, respectively, or amino acid sequences of SEQ ID NOs: 1 to 3 , respectively modified by deletion, substitution, or addition of one or several amino acids and a light-chain variable region comprising amino acid sequences of SEQ ID NOs: 4 to 6, respectively, or amino acid sequences of SEQ ID NOs: 4 to 6, respectively, modified by deletion, substitution, or addition of one or several amino acids, or CDR1 to CDR3 compete with an antibody having a heavy-chain variable region comprising amino acid sequences of SEQ ID NOs: 1 to 3, respectively, and a light-chain variable region comprising C amino acid sequences of SEQ ID NOs: 4 to 6, respectively, when bound to human DNAM-1.

[14] The anti-human DNAM-1 monoclonal antibody or the fragment thereof according to any one of [10] to [13], the CDR1 to CDR3 have a heavy-chain variable region comprising amino acid sequences of SEQ ID NOs: 1 to 3, respectively, or amino acid sequences of SEQ ID NOs: 1 to 3, respectively, modified by deletion, substitution, or addition of one or several amino acids and the CDR1 to CDR3 have a light-chain variable region comprising amino acid sequences of SEQ ID NOs: 4 to 6, respectively, or amino acid sequences of SEQ ID NOs: 4 to 6, respectively, modified by deletion, substitution, or addition of one or several amino acids.

[15] The anti-human DNAM-1 monoclonal antibody or the fragment thereof according to any one of [10] to [14], wherein the CDR1 to CDR3 have a heavy-chain variable region comprising amino acid sequences of SEQ ID NOs: 1 to 3, respectively, and a light-chain variable region comprising amino acid sequences of SEQ ID NOs: 4 to 6, respectively.

[16] The anti-human DNAM-1 monoclonal antibody or the fragment thereof according to any one of [10] to [15], wherein the antibody or a fragment thereof include a heavy-chain variable region comprising an amino acid sequence of SEQ ID NO: 7 or an amino acid sequence of SEQ ID NO: 7 modified by deletion, substitution, or addition of one or several amino acids and a light-chain variable region comprising an amino acid sequence of SEQ ID NO: 8 or an amino acid sequence of SEQ ID NO: 8 modified by deletion, substitution, or addition of one or several amino acids.

[17] The anti-human DNAM-1 monoclonal antibody or the fragment thereof according to [16], wherein the antibody or a fragment thereof include a heavy-chain variable region comprising an amino acid sequence of SEQ ID NO: 7 and a light-chain variable region comprising an amino acid sequence of SEQ ID NO: 8.

[18] The anti-human DNAM-1 monoclonal antibody or the fragment thereof according to any one of [10] to [14], wherein the antibody or a fragment thereof include a heavy-chain variable region comprising an amino acid sequence of SEQ ID NO: 9 or an amino acid sequence of SEQ ID NO: 9 modified by deletion, substitution, or addition of one or several amino acids and a light-chain variable region comprising an amino acid sequence of SEQ ID NO: 10 or an amino acid sequence of SEQ ID NO: 10 modified by deletion, substitution, or addition of one or several amino acids.

[19] The anti-human DNAM-1 monoclonal antibody or the fragment thereof according to [18], wherein the antibody or a fragment thereof include a heavy-chain variable region comprising an amino acid sequence of SEQ ID NO: 9 and a light-chain variable region comprising an amino acid sequence of SEQ ID NO: 10.

[20] A nucleic acid coding for the anti-human DNAM-1 monoclonal antibody or the fragment thereof according any one of [10] to [19].

[21] A vector comprising the nucleic acid according to [20].

[22] A transformant according to the vector according to [21].

(1) An anti-human DNAX accessory molecule-1 (DNAM-1) monoclonal antibody or a fragment thereof (antibody fragment), having a heavy-chain variable region comprising CDR1 to CDR3 having amino acid sequences of SEQ ID NOs: 1 to 3, respectively, or amino acid sequences of SEQ ID NOs: 1 to 3, respectively, modified by deletion, substitution, or addition of one or several amino acids and a light-chain variable region comprising CDR1 to CDR3 having amino acid sequences of SEQ ID NOs: 4 to 6 respectively, or amino acid sequences of SEQ ID NOs: 4 to 6 respectively modified by deletion, substitution, or addition of one or several amino acids.

(2) The anti-human DNAM-1 monoclonal antibody or a fragment thereof according to (1), having a heavy-chain variable region comprising CDR1 to CDR3 having amino acid sequences of SEQ ID NOs: 1 to 3 respectively, and a light-chain variable region comprising CDR1 to CDR3 having amino acid sequences of SEQ ID NOs: 4 to 6 respectively.

(3) The anti-human DNAM-1 monoclonal antibody or a fragment thereof according to (1) or (2), having a heavy-chain variable region comprising an amino acid sequence of SEQ ID NO: 7 or an amino acid sequence of SEQ ID NO: 7 modified by deletion, substitution, or addition of one or several amino acids and a light-chain variable region comprising an amino acid sequence of SEQ ID NO: 8 or an amino acid sequence of SEQ ID NO: 8 modified by deletion, substitution, or addition of one or several amino acids.

(4) The anti-human DNAM-1 monoclonal antibody or a fragment thereof according to any one of (1) to (3), having a heavy-chain variable region comprising an amino acid sequence of SEQ ID NO: 7 and a light-chain variable region comprising an amino acid sequence of SEQ ID NO: 8.

(5) A nucleic acid coding for the anti-human DNAM-1 monoclonal antibody or a fragment thereof according to any one of (1) to (4).

(6) A recombinant vector having the nucleic acid according to (5).

(7) A transformant having the recombinant vector according to (6).

(8) An immunosuppressant including the anti-human DNAM-1 monoclonal antibody or a fragment thereof according to any one of (1) to (4) as an active ingredient.

(9) The immunosuppressant according to (8) used for preventing or treating graft-versus-host disease.

(10) The immunosuppressant according to (8) used for preventing or treating transplant rejection.

Advantageous Effects of Invention

According to the present invention, a technology for reducing human immune responses may be provided.

BRIEF DESCRIPTION OF DRAWINGS

FIG. 1 is a diagram illustrating the alignment of the amino acid sequences of the heavy chains of anti-human DNAM-1 monoclonal antibody Nos. 1 to 6. (SEQ ID NOS: 7, 9, 11, 13, 15, and 17)

FIG. 2 is a diagram illustrating the alignment of the amino acid sequences of the light chains of anti-human DNAM-1 monoclonal antibody Nos. 1 to 6. (SEQ ID NOS: 8, 10, 12, 14, 16, and 18)

DETAILED DESCRIPTION OF EMBODIMENTS OF THE PRESENT INVENTION

[Regulatory T Cell Activator]

Figure 3:
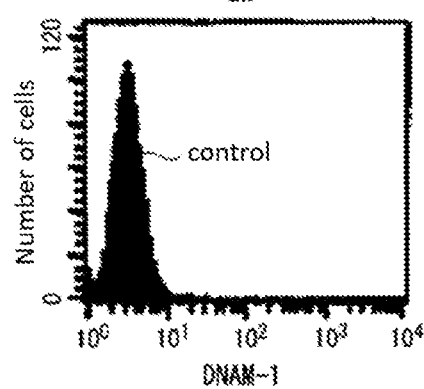
FIGS. 3(a) to 3(d) are graphs illustrating the results obtained in Test example 2.
Figure 3:
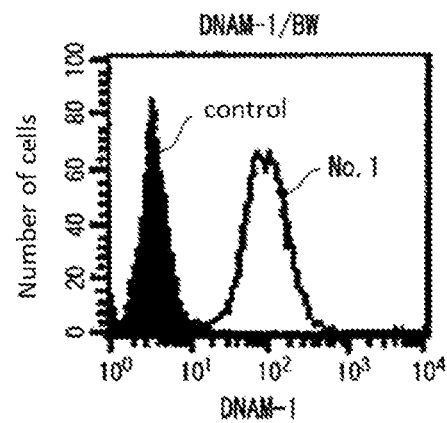
Figure 3:
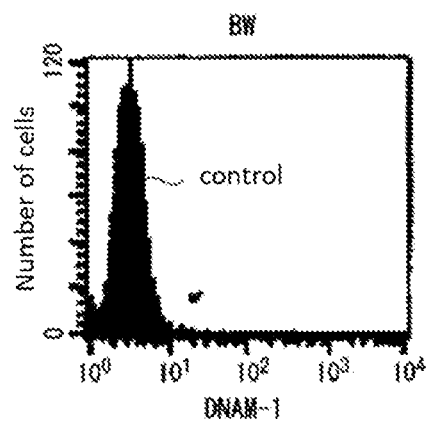
Figure 3:
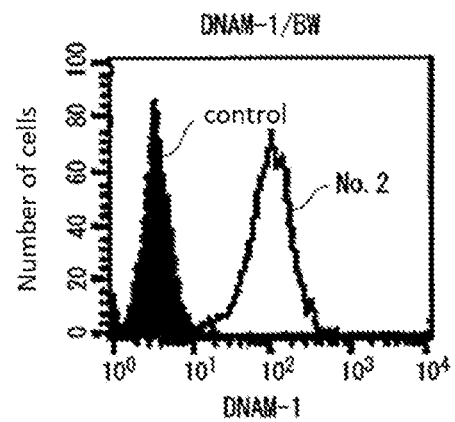

An embodiment of the present invention provides a regulatory T cell activator comprising a substance that inhibits the binding between DNAM-1 and CD155.

As described in Examples below, the inventors found that regulatory T cells can be activated by inhibiting the binding between DNAM-1 and CD155. Therefore, a substance that inhibits the binding between DNAM-1 and CD155 can be used for activating regulatory T cells.

Examples of the substance that inhibits the binding between DNAM-1 and CD155 include a substance that specifically binds to DNAM-1, an agent that inhibits expression of DNAM-1, a substance that specifically binds to CD155, and an agent that inhibits expression of CD155.

The substance that specifically binds to DNAM-1 and the substance that specifically binds to CD155 may be any substance capable of inhibiting the binding between DNAM-1 and CD155. Examples of such a substance include an antibody, an antibody fragment, and an aptamer. The antibody may be produced by immunizing an animal, such as a mouse, or by screening an antibody library, such as a phage library. Examples of an antibody fragment include F(ab')2, Fab', Fab, Fv, and scFv. Examples of an aptamer include a nucleic acid aptamer, and a peptide aptamer.

The substance that specifically binds to DNAM-1 may be solubilized CD155. Examples of a solubilized CD155 include a fusion protein formed by the fusion of CD155 with an antibody constant region and the like. The substance that specifically binds to CD155 may be a solubilized DNAM-1. Examples of a solubilized DNAM-1 include a fusion protein formed by the fusion of DNAM-1 with an antibody constant region and the like.

The agent that inhibits the expression of DNAM-1 and the agent that inhibits the expression of CD155 may be any substance capable of reducing the expression of DNAM-1 or CD155 and consequently inhibiting the binding between DNAM-1 and CD155. Examples of such a substance include siRNA, shRNA, miRNA, ribozyme, antisense nucleic acid, and a low-molecular compound. siRNA, shRNA, miRNA, ribozyme, and antisense nucleic acid may include various chemical modifications in order to enhance stability and activity. For example, a phosphate residue may be replaced with a chemically modified phosphate residue, such as phosphorothioate, methyl phosphonate, or phosphorodithioate, in order to prevent decomposition by a hydrolase, such as nuclease. At least a portion thereof may be composed of a nucleic acid analogue, such as peptide nucleic acid (PNA).

A regulatory T cell is a type of T cells and also known as Treg. It is being clarified that regulatory T cells are responsible for the inhibitory control of immune responses. Examples of regulatory T cells include a $CD4^+$ $CD25^+$ T cell, a $Foxp3^-$ $CD25^+$ T cell, and a $CD4^+$ $FOxp3^+$ cell.

The term "activation of regulatory T cells" used herein refers to, for example, an increase in the number of regulatory T cells, an increase in the amount of inhibitory cytokine, such as TGF-β or IL-10 expressed by regulatory T cells, inhibition of immune responses by the T cells, or inhibition of general immune responses.

The regulatory T cell activator according to this embodiment may be used for preventing or treating a disease, the symptoms of which can be reduced by the activation of regulatory T cells. Examples of such a disease include graft-versus-host disease, transplant rejection, an autoimmune disease, fibrosis, inflammatory enteritis, and an allergy.

Examples of autoimmune diseases include rheumatism, Type I diabetes mellitus, and autoimmune encephalomyelitis. Fibrosis is a disease in which the tissue of an organ, such as a lung, a heart, a liver, or a kidney, is replaced with type I collagen or the like. Examples of fibrosis include cirrhosis, diabetic nephropathy, and pulmonary fibrosis. Examples of an allergy include allergic rhinitis and atopic dermatitis.

The regulatory T cell activator according to this embodiment may be, for example, a substance that specifically binds to DNAM-1. The specific binding substance may be an antibody or fragment thereof. The DNAM-1 may be DNAM-1 of any species whose regulatory T cells are to be activated. For example, the DNAM-1 may be human DNAM-1. In other words, the regulatory T cell activator according to this embodiment may be an anti-human DNAM-1 antibody or a fragment thereof.

The anti-human DNAM-1 antibody or a fragment thereof preferably has reactivity with which human DNAM-1 forcibly expressed on surfaces of $1\times10^5$ lymphocytes can be saturated when the antibody or a fragment thereof is reacted with the human DNAM-1 with 100 ng or less, preferably 80 ng or less, more preferably 50 ng or less, further preferably 40 ng or less, and particularly preferably 30 ng or less of the anti-human DNAM-1 antibody or a fragment thereof in terms of the full-length of the IgG antibody. As described in Examples below, an anti-human DNAM-1 antibody having such reactivity has a high ability to activate regulatory T cells.

In the case where the target antibody is, for example, an antibody fragment, the reactivity of the antibody fragment is calculated by converting the full-length of the IgG antibody. In this case, the mass conversion may be made, for example, on the basis of the molecular weights of the antibody fragment and the full-length of the IgG antibody.

When human DNAM-1 forcibly expressed on surfaces of $1\times10^5$ lymphocytes is saturated with 1000 ng of the fusion protein formed human CD155 with an IgG antibody constant region and then the anti-human DNAM-1 antibody or a fragment thereof is reacted with the lymphocytes, the anti-human DNAM-1 antibody or the fragment thereof used preferably as a regulatory T cell activator according to this embodiment may have reactivity which inhibits the binding between the fusion protein and human DNAM-1 molecule on the surface of the lymphocytes with 500 ng or less, preferably 400 ng or less, more preferably 300 ng or less, further preferably 200 ng or less, and particularly preferably 100 ng or less of the anti-human DNAM-1 antibody or a fragment thereof in terms of the mass of the full-length of the IgG antibody.

In other words, an anti-human DNAM-1 antibody having such reactivity is capable of breaking the binding between DNAM-1 and CD155 even when DNAM-1 has been bound to CD155. As described in Examples below, an anti-human DNAM-1 antibody having such reactivity has a high ability to activate regulatory T cells.

The expression "completely inhibit" used herein means that can be substantially completely inhibited. For example, in the case where human DNAM-1 molecule present on the surfaces of $1\times10^5$ lymphocytes on which human DNAM-1 is forcibly expressed are saturated with 1000 ng of a fusion protein formed by the fusion of human CD155 with an IgG antibody constant region and then the lymphocytes is reacted with, 80% or more, preferably 90% or more, more preferably 95% or more, and further preferably 99% or more of fusion protein bound to the surfaces of the lymphocytes is dissociated and human DNAM-1 present on the surfaces of the lymphocytes is bound.

The regulatory T cell activator according to this embodiment may be an anti-human CD155 antibody or a fragment thereof.

In the regulatory T cell activator according to this embodiment, the anti-human DNAM-1 antibody or the fragment thereof, or the anti-human CD155 antibody or a fragment thereof is preferably a human type antibody or a fragment thereof.

When the regulatory T cell activator is a human type antibody or a fragment of thereof, the occurrence of side effects, such as anaphylactic shock, can be reduced even when it is administered to a human because of low immunogenicity. Examples of a human type antibody include a chimeric antibody, a humanized antibody, a fully human type antibody and the like.

The term "chimeric antibody" used herein refers to an antibody including a variable region derived from a nonhuman animal and a constant region at least a part of which is derived from a human. The term "humanized antibody" used herein refers to an antibody in which only the complementarity determining regions (CDRs) of the heavy and light chains are derived from a nonhuman animal and the constant region and the framework region are derived from a human. The term "fully human type antibody" used herein refers to an antibody the entirety of which including the complementarity determining regions is derived from a human.

In the regulatory T cell activator according to this embodiment, the anti-human DNAM-1 antibody or a fragment thereof may include a heavy-chain variable region comprising CDR1 to CDR3 having amino acid sequences of SEQ ID NOs: 1 to 3, respectively, or amino acid sequences of SEQ ID NOs: 1 to 3, respectively, modified by deletion, substitution, or addition of one or several amino acids, and a light-chain variable region comprising CDR1 to CDR3 having amino acid sequences of SEQ ID NOs: 4 to 6 respectively, or amino acid sequences of SEQ ID NOs: 4 to 6 respectively modified by deletion, substitution, or addition of one or several amino acids.

The term "several" used herein refers to 4, 3, or 2 when referring to CDR1 or CDR2 of the heavy-chain variable region. The term "several" used herein refers to 2 when referring to CDR3 of the heavy-chain variable region. The term "several" used herein refers to 4, 3, or 2 when referring to CDR1 or CDR3 of the light-chain variable region. The term "several" used herein refers to 2 when referring to CDR2 of the light-chain variable region.

Examples of an antibody that includes a heavy-chain variable region comprising CDR1 to CDR3 having amino acid sequences of SEQ ID NOs: 1 to 3, respectively, and a light-chain variable region comprising CDR1 to CDR3 having amino acid sequences of SEQ ID NOs: 4 to 6, respectively, include the monoclonal antibody No. 1 described in Examples below and an antibody produced by humanizing the monoclonal antibody No. 1.

The anti-human DNAM-1 antibody is not limited to the monoclonal antibody No. 1; any anti-human DNAM-1 antibody having reactivity comparable to or higher than that of the monoclonal antibody No. 1 may be used as a regulatory T cell activator according to this embodiment. That is, the anti-human DNAM-1 antibody may be an antibody that includes a heavy-chain variable region comprising CDR1 to CDR3 having amino acid sequences of SEQ ID NOs: 1 to 3 respectively modified by deletion, substitution, or addition of one or several amino acids, and a light-chain variable region comprising CDR1 to CDR3 having amino acid sequences of SEQ ID NOs: 4 to 6 respectively modified by deletion, substitution, or addition of one or several amino acids. Examples of such an antibody include the monoclonal antibody Nos. 2 to 6 and antibodies produced by humanizing the monoclonal antibody Nos. 2 to 6 described in Examples below.

The anti-human DNAM-1 antibody or a fragment thereof may also be an antibody or a fragment thereof which competes with an antibody that includes a heavy-chain variable region comprising CDR1 to CDR3 having amino acid sequences of SEQ ID NOs: 1 to 3 respectively and a light-chain variable region comprising CDR1 to CDR3 having amino acid sequences of SEQ ID NOs: 4 to 6 respectively when bound to human DNAM-1. In other words, the anti-human DNAM-1 antibody may be an antibody that competes with the monoclonal antibody No. 1 described in Examples below when bound to human DNAM-1. An antibody that competes with the monoclonal antibody No. 1 has reactivity comparable to or higher than that of the monoclonal antibody No. 1 when bound to human DNAM-1.

The expression, "a target antibody competes", means that, for example, when human DNAM-1 molecule present on the surfaces of $1 \times 10^5$ lymphocytes in which human DNAM-1 is forcibly expressed are reacted with the monoclonal antibody No. 1 described in Examples below and then a target molecule is reacted with the lymphocytes, at least a part of the binding between the monoclonal antibody No. 1 and the human DNAM-1 may be dissociated and the human DNAM-1 may be bound.

The expression "at least a part" used herein may refer to 10% or more, 30% or more, 50% or more, 70% or more, and 90% or more of the total amount of human DNAM-1 present on the surfaces of the $1 \times 10^5$ lymphocytes.

[Pharmaceutical Composition for Activation of Regulatory T Cells]

Another embodiment of the present invention provides a pharmaceutical composition for activation of regulatory T cells which includes the above-described regulatory T cell activator and a pharmaceutically acceptable carrier.

Examples of the pharmaceutically acceptable carrier include carriers commonly used for producing drugs, such as a vehicle, a stabilizer, and an injection solvent. Examples of the injection solvent include an isotonic solution containing an adjuvant such as physiological salt solution, glucose, D-sorbitol, D-mannose, D-mannitol, or sodium chloride.

The pharmaceutical composition according to this embodiment may further include an additive other than the above-described regulatory T cell activator or the pharmaceutically acceptable carrier. Examples of the other additive include a pH regulator, a viscosity improver, a colorant, and a steroid and an immunosuppressant that have been used for treating graft-versus-host disease or transplant rejection.

Examples of the dosage form of the pharmaceutical composition according to this embodiment include, but are not limited to, a lyophilized drug, a powdered drug, a solution drug containing a pH-controlled buffer solution, and a microencapsulated drug for injection.

The pharmaceutical composition according to this embodiment is administered to a patient for example, in the form of an injection or an instillation drug, or by intravenous administration or the like. The dose of the pharmaceutical composition, the route of administration, and the recipe of the pharmaceutical composition may be determined appropriately in accordance with the symptoms, weight, age, sex, and the like of the patient.

The dose of the pharmaceutical composition according to this embodiment varies with the symptoms, weight, age, sex, and the like of the patient and cannot be determined unconditionally. The pharmaceutical composition according to this embodiment may be administered to a human patient in need of treatment once to a few times a day in certain amounts such that the amount of active ingredient (the substance that inhibits binding the between DNAM-1 and CD155) of the pharmaceutical composition per kilogram of body weight is, for example, 1 µg to 100 mg or 50 µg to 50 mg per dose.

[Anti-human DNAM-1 Monoclonal Antibody or Fragment thereof]

Still another embodiment of the present invention provides an anti-human DNAM-1 monoclonal antibody or a fragment thereof which is capable of saturating human DNAM-1 molecule forcibly expressed on surfaces of $1 \times 10^5$ lymphocytes when reacted with the human DNAM-1, with 100 ng or less, preferably 80 ng or less, more preferably 50 ng or less, further preferably 40 ng or less, and particularly preferably 30 ng or less of the anti-human DNAM-1 monoclonal antibody or a fragment thereof in terms of the full-length of the IgG antibody.

As described in Examples below, an anti-human DNAM-1 antibody having such reactivity is useful for, for example, the activation of regulatory T cells and the mitigation of symptoms of graft-versus-host disease, transplant rejection, autoimmune disease, fibrosis, inflammatory enteritis, or the like.

In the case where the antibody whose reactivity is to be determined is, for example, an antibody fragment, the reactivity of the antibody may be determined in terms of the the full length of the IgG antibody. In this case, the mass of the antibody fragment may be converted into the full length of the IgG antibody on the basis of the molecular weights of the antibody fragment and the full length of the IgG antibody. The anti-human DNAM-1 monoclonal antibody or a fragment thereof according to this embodiment may be other than known antibodies or fragments thereof.

When human DNAM-1 forcibly expressed on surfaces of $1 \times 10^5$ lymphocytes is saturated with 1000 ng of the fusion protein formed human CD155 with an IgG antibody constant region and then the anti-human DNAM-1 antibody or a fragment thereof is reacted with the lymphocytes, the anti-human DNAM-1 antibody or the fragment thereof according to this embodiment may have reactivity which inhibits the binding between the fusion protein and human DNAM-1 molecule on the surface of the lymphocytes with 500 ng or less, preferably 400 ng or less, more preferably 300 ng or less, further preferably 200 ng or less, and particularly preferably 100 ng or less of the anti-human DNAM-1 antibody or a fragment thereof in terms of the full-length of the IgG antibody.

In other words, an anti-human DNAM-1 antibody having such reactivity is capable of breaking the binding between DNAM-1 and CD155 even when DNAM-1 has been bound to CD155. The meaning of the expression "completely inhibit" used herein is the same as described above.

The anti-human DNAM-1 monoclonal antibody or a fragment thereof according to this embodiment may be a human type antibody or a fragment thereof. The human type antibody is the same as described above.

The anti-human DNAM-1 monoclonal antibody or a fragment thereof according to this embodiment, may include a heavy-chain variable region comprising CDR1 to CDR3 having amino acid sequences of SEQ ID NOs: 1 to 3 respectively, or amino acid sequences of SEQ ID NOs: 1 to 3 respectively modified by deletion, substitution, or addition of one or several amino acids, and a light-chain variable region comprising CDR1 to CDR3 having amino acid sequences of SEQ ID NOs: 4 to 6 respectively, or amino acid sequences of SEQ ID NOs: 4 to 6 respectively modified by deletion, substitution, or addition of one or several amino acids.

The expression "several" used when referring to CDR1 or CDR2 of the heavy-chain variable region means 4, 3, or 2. The expression "several" used when referring to CDR3 of the heavy-chain variable region means 2. The expression "several" used when referring to CDR1 or CDR3 of the light-chain variable region means 4, 3, or 2. The expression "several" used when referring to CDR2 of the light-chain variable region means 2.

The term "antibody fragment" used herein refers to, for example, Fab, F(ab')2, and single-chain Fv (scFv) produced by joining a heavy-chain variable region and a light-chain variable region with an adequate linker. Examples of a linker of scFv include peptides such as $(GGGGS)_3$ (SEQ ID NO: 21).

As described in Examples below, the anti-human DNAM-1 monoclonal antibody or the fragment thereof according to this embodiment suitably binds to human DNAM-1 protein and thereby reducing the immune responses of human in vivo and in vitro. Accordingly, the anti-human DNAM-1 monoclonal antibody or the fragment thereof according to this embodiment can be used as an immunosuppressant.

The anti-human DNAM-1 antibody or a fragment thereof according to this embodiment may also be an antibody or a fragment thereof which competes with an antibody that includes a heavy-chain variable region comprising CDR1 to CDR3 having amino acid sequences of SEQ ID NOs: 1 to 3 respectively and a light-chain variable region comprising CDR1 to CDR3 having amino acid sequences of SEQ ID NOs: 4 to 6 respectively when bound to human DNAM-1. In other words, the anti-human DNAM-1 antibody may be an antibody that competes with the monoclonal antibody No. 1 described in Examples below when bound to human DNAM-1. An antibody that competes with the monoclonal antibody No. 1 has reactivity comparable to or higher than that of the monoclonal antibody No. 1 when bound to human DNAM-1. The competition of the antibodies is the same as described above.

The anti-human DNAM-1 monoclonal antibody or a fragment thereof may include a heavy-chain variable region including CDR1 to CDR3 having the amino acid sequences of SEQ ID NOs: 1 to 3, respectively, and a light-chain variable region including CDR1 to CDR3 having the amino acid sequences of SEQ ID NOs: 4 to 6, respectively. Examples of the above antibody include the monoclonal antibody No. 1 described in Examples below and an antibody produced by humanizing the monoclonal antibody No. 1.

The anti-human DNAM-1 monoclonal antibody or a fragment thereof may include a heavy-chain variable region having the amino acid sequence of SEQ ID NO: 7 and a light-chain variable region having the amino acid sequence of SEQ ID NO: 8. Examples of such an antibody include the monoclonal antibody No. 1 described in Examples below and an antibody produced by humanizing the monoclonal antibody No. 1.

The anti-human DNAM-1 monoclonal antibody or a fragment thereof may include a heavy-chain variable region having the amino acid sequence of SEQ ID NO: 9 and a light-chain variable region having the amino acid sequence of SEQ ID NO: 10. Examples of such an antibody include the monoclonal antibody No. 2 described in Examples below and an antibody produced by humanizing the monoclonal antibody No. 2.

The anti-human DNAM-1 monoclonal antibody or a fragment thereof may include a heavy-chain variable region having the amino acid sequence of SEQ ID NO: 7 modified by deletion, substitution, or addition of one or several amino acids and a light-chain variable region having the amino acid sequence of SEQ ID NO: 8 modified by deletion, substitution, or addition of one or several amino acids, as long as the anti-human DNAM-1 monoclonal antibody or a fragment thereof is reactive with human DNAM-1.

The anti-human DNAM-1 monoclonal antibody or a fragment thereof may include a heavy-chain variable region having the amino acid sequence of SEQ ID NO: 9 modified by deletion, substitution, or addition of one or several amino acids and a light-chain variable region having the amino acid sequence of SEQ ID NO: 10 modified by deletion, substitution, or addition of one or several amino acids, as long as the anti-human DNAM-1 monoclonal antibody or a fragment thereof is reactive with human DNAM-1.

The expression "several" used when referring to the heavy-chain variable region or the light variable region means 15, 14, 13, 12, 11, 10, 9, 8, 7, 6, 5, 4, 3, or 2. Examples of such an antibody include the monoclonal antibody Nos. 3 to 6 and antibodies produced by humanizing the monoclonal antibody Nos. 3 to 6 described in Examples below.

[Nucleic Acid Coding for Anti-human DNAM-1 Monoclonal Antibody or Fragment thereof]

Yet another embodiment of the present invention provides a nucleic acid coding for the above-described anti-human DNAM-1 monoclonal antibody or a fragment thereof.

Examples of such a nucleic acid include a gene coding for the heavy-chain variable region of the above-described anti-human DNAM-1 monoclonal antibody, a gene coding for the light-chain variable region of the anti-human DNAM-1 monoclonal antibody, a gene coding for the heavy-chain variable region and a part of the constant region of the anti-human DNAM-1 monoclonal antibody, a gene coding for the light-chain variable region and a part of the constant region of the anti-human DNAM-1 monoclonal antibody, a gene coding for the full length of the heavy chain of the anti-human DNAM-1 monoclonal antibody, a gene coding for the full length of the light-chain of the anti-human DNAM-1 monoclonal antibody, and a gene coding for scFv formed by fusing the heavy-chain variable regions and light-chain variable region of the anti-human DNAM-1 monoclonal antibody with an adequate linker.

The gene coding for the heavy-chain variable region may be a gene having the base sequence of SEQ ID NO: 19. The gene coding for the light-chain variable region may be a gene having the base sequence of SEQ ID NO: 20.

The gene coding for the heavy-chain variable region may be a gene coding for a heavy-chain variable region including CDR1 to CDR 3 having the amino acid sequences of SEQ ID NOs: 1 to 3, respectively, and a framework region other than CDRs may be a gene which is derived from a nonmouse antibody. The gene coding for the light-chain variable region may be a gene coding for a light-chain variable region including CDR1 to CDR 3 having the amino acid sequences of SEQ ID NOs: 4 to 6, respectively, and a framework region other than CDRs may be a gene which is derived from a nonmouse antibody. Examples of the nonmouse antibody include a human type antibody.

The nucleic acid according to this embodiment is preferably a combination of the gene coding for the heavy-chain variable region of the anti-human DNAM-1 monoclonal antibody or a gene derived therefrom and the gene coding for the light-chain variable region of the anti-human DNAM-1 monoclonal antibody or a gene derived therefrom.

Examples of the gene derived from the gene coding for the heavy-chain variable region include a gene coding for a heavy-chain variable region including CDR1 to CDR 3 having the amino acid sequences of SEQ ID NOs: 1 to 3, respectively, and a framework region other than CDRs which is derived from a nonmouse antibody. Similarly, examples of the gene derived from the gene coding for the light-chain variable region include a gene coding for a light-chain variable region including CDR1 to CDR 3 having the amino acid sequences of SEQ ID NOs: 4 to 6, respectively, and a framework region other than CDRs which is derived from a nonmouse antibody.

[Vector]

Still another embodiment of the present invention provides a recombinant vector including the above-described nucleic acid. The recombinant vector according to this embodiment may be an expression vector. When the vector according to this embodiment is an expression vector, it is possible to produce the anti-human DNAM-1 monoclonal antibody or a fragment thereof by introducing the vector into the host and causing the gene to express.

In the recombinant vector according to this embodiment, a DNA coding for a tag sequence such as a histidine-tag, a FLAG-tag, or a GST-tag may be attached to the 5' end or 3' end of the above-described nucleic acid. Examples of the expression vector include a cell vector that expresses the anti-human DNAM-1 monoclonal antibody or a fragment thereof in host cells and a cell-free vector that expresses the anti-human DNAM-1 monoclonal antibody or a fragment thereof in a protein translation system that includes a component having a protein synthesis ability which is extracted from suitable cells.

The cell vector may be any known expression vector suitable for host cells. In the case where Escherichia coli is used as a host, examples of the vector include ColE plasmids, such as pBR322 derivative; pACYC plasmids with a p15A origin; pSC plasmids; mini-F plasmids derived from F factor, such as Bac plasmids; and expression vectors including a tryptophan promoter (e.g., trc or tac), a lac promoter, a T7 promoter, a T5 promoter, a T3 promoter, a SP6 promoter, an arabinose-inducible promoter, a cold shock promoter, or a tetracycline-inducible promoter. In the case where the host is other than Escherichia coli, examples of the vector include pAUR plasmids used for expression on yeast, plEx plasmids used for expression of insect cells, and pBApo-CMV plasmids used for expression of the animal cells.

Examples of the cell-free vector include an expression vector having the T7 promoter and an expression vector having the T3 promoter which are described above as examples of the cell vector; and wheat cell-free protein synthesis vector, such as a pEU plasmid having a SP6 promoter or a T7 promoter.

When a protein is synthesized using a cell-free vector, first, mRNA is synthesized by a transcription system responsible for the transcription of SesA gene. Examples of the transcription system include known transcription systems capable of performing the transcription using RNA polymerase. Examples of the RNA polymerase include T7 RNA polymerase and SP6 polymerase.

Subsequently, mRNA is translated using a cell-free protein synthesis system, that is, a translation system, in order to synthesis a protein. This system includes various elements required for translation, such as ribosome, a translation initiation factor, a translation elongation factor, a release factor, and aminoacyl-tRNA synthetase. Examples of the above protein translation system include a E. coli extract, a rabbit reticulocyte extract, a wheat germ extract, and a reconstituted cell-free protein synthesis system that includes only the factors required by the translation which have been purified individually.

The anti-human DNAM-1 monoclonal antibody or a fragment thereof can be used by purification from the protein synthesized using the cell vector or the cell-free vector. Examples of the purification method include a method in which Protein A, Protein G, or the like is used. In the case where the expression vector is designed to express a tag sequence, such as a histidine-tag, at the N-end or C-end of a target protein, the purification may be performed using an affinity column with a substance, such as nickel or cobalt, having an affinity for the tag. The purity of the anti-human DNAM-1 monoclonal antibody or a fragment thereof can be increased by performing the purification using ion-exchange chromatography, gel-permeation chromatography, and the like in combination appropriately.

[Transformant]

Yet another embodiment of the present invention provides a transformant including the above-described recombinant vector. The anti-human DNAM-1 monoclonal antibody or a fragment thereof can be produced by using the transformant according to this embodiment or a medium or the like of the transformant.

The transformant according to this embodiment can be produced by introducing the above-described recombinant vector into a host. Examples of the transformant include culture cells, such as *Escherichia coli*, yeast, plant cells, insect cells, and animal cells, into which the above-described recombinant vector has been introduced; a living insect, such as a silkworm, into which the above-described recombinant vector has been introduced; and a plant body, such as a tobacco and the like, into which the above-described recombinant vector has been introduced.

The introduction of the recombinant vector into the host (transformation) may be performed by a publicly known method, such as a competent cell method in which cells treated with calcium are used and electroporation. Instead of using a plasmid vector, the transformation may alternatively be performed by infecting the host with a phage vector, a virus vector, or the like.

[Immunosuppressant]

Still another embodiment of the present invention provides an immunosuppressant that includes the above-described anti-human DNAM-1 monoclonal antibody or a fragment thereof, serving as an active ingredient.

As described in Examples below, the immunosuppressant according to this embodiment is capable of inhibiting the proliferation of the $CD8^+$ T cells in a mixed lymphocyte reaction (MLR) assay.

Furthermore, as described in Examples below, it was confirmed in a mouse model of graft-versus-host disease that the immunosuppressant according to this embodiment is effective in preventing and treating graft-versus-host disease.

Accordingly, the immunosuppressant according to this embodiment can be a drug for preventing or treating graft-versus-host disease. The immunosuppressant according to this embodiment can be a drug for preventing or treating transplant rejection.

The immunosuppressant according to this embodiment may be a pharmaceutical composition that includes a pharmaceutically acceptable carrier and other additives. Examples of the pharmaceutically acceptable carrier include a vehicle, a stabilizer, and an injection solvent. Examples of the injection solvent include an isotonic solution containing an adjuvant such as a physiological saline solution, glucose, D-sorbitol, D-mannose, D-mannitol, or sodium chloride. Examples of the other additives include a pH regulator, a viscosity improver, a colorant, and a steroid and an immunosuppressant that have been used for treating graft-versus-host disease or transplant rejection.

Examples of the dosage form of the immunosuppressant according to this embodiment and the above-described pharmaceutical composition include, but are not limited to, a lyophilized drug, a powdered drug, a pH-controlled solution drug containing a buffer solution, and a microencapsulated drug for injection.

The immunosuppressant according to this embodiment or the above-described pharmaceutical composition is administered to a patient in the form of an injection, an instillation drug, or the like by intravenous administration or the like. The dose of the immunosuppressant or the pharmaceutical composition, the route of administration, and the recipe of the immunosuppressant or the pharmaceutical composition may be determined appropriately in accordance with the symptoms, weight, age, sex, etc. of the patient.

The dose of the immunosuppressant according to this embodiment or the above-described pharmaceutical composition varies with the symptoms, weight, age, sex, etc. of the patient and cannot be determined unconditionally. The immunosuppressant or the pharmaceutical composition may be administered to a human patient in need of treatment once to a few times a day in certain amounts such that the amount of active ingredient (the anti-human DNAM-1 monoclonal antibody or a fragment thereof) per kilogram of body weight is, for example, 1 µg to 100 mg or 50 µg to 50 mg per dose.

Other Embodiments

Another embodiment of the present invention provides a method for activating regulatory T cells which includes administering an effective amount of substance that inhibits the binding between DNAM-1 and CD155 to a patient in need of treatment. Examples of the substance that inhibits the binding between DNAM-1 and CD155 are as described above.

Still another embodiment of the present invention provides a substance that inhibits the binding between DNAM-1 and CD155 which is used for activating regulatory T cells. Examples of the substance that inhibits the binding between DNAM-1 and CD155 are as described above.

Yet another embodiment of the present invention provides a substance that inhibits the binding between DNAM-1 and CD155 which is used for producing a regulatory T cell activator. Examples of the substance that inhibits the binding between DNAM-1 and CD155 are as described above.

Still another embodiment of the present invention provides a method for preventing or treating graft-versus-host disease, transplant rejection, an autoimmune disease, fibrosis, inflammatory enteritis, or an allergy which includes administering an effective amount of substance that inhibits the binding between DNAM-1 and CD155 to a patient in need of treatment. Examples of the substance that inhibits the binding between DNAM-1 and CD155 are as described above.

Yet another embodiment of the present invention provides a substance that inhibits the binding between DNAM-1 and CD155 which is used for preventing or treating graft-versus-host disease, transplant rejection, an autoimmune disease, fibrosis, inflammatory enteritis, or an allergy. Examples of the substance that inhibits the binding between DNAM-1 and CD155 are as described above.

Still another embodiment of the present invention provides a substance that inhibits the binding between DNAM-1 and CD155 which is used for producing a drug for preventing or treating graft-versus-host disease, transplant rejection, an autoimmune disease, fibrosis, inflammatory enteritis, or an allergy. Examples of the substance that inhibits the binding between DNAM-1 and CD155 are as described above.

Yet another embodiment of the present invention provides a method for treating or preventing graft-versus-host disease or transplant rejection which includes administering an effective amount of the above-described anti-human DNAM-1 monoclonal antibody or a fragment thereof to a patient in need of treatment.

Still another embodiment of the present invention provides the above-described anti-human DNAM-1 monoclonal antibody or a fragment thereof which is used for treating or preventing graft-versus-host disease or transplant rejection.

Yet another embodiment of the present invention provides the above-described anti-human DNAM-1 monoclonal antibody or a fragment thereof which is used for producing a drug for treating or preventing graft-versus-host disease or transplant rejection.

EXAMPLES

The present invention is described further in detail with reference to Test examples below. The present invention is not limited by Test examples below.

Test Example 1

(Preparation of Anti-Human DNAM-1 Monoclonal Antibody)

Human DMAM-1 gene was introduced into a BW5147 cell line, which is derived from mouse lymphocytes, to express human DMAM-1 protein. A mouse was immunized using the cells as an antigen, and a hybridoma was prepared in the usual manner. From the resulting hybridoma line, clones that produced a specific one of the anti-human DNAM-1 monoclonal antibody Nos. 1 to 6 were obtained in accordance with reactivity with the human DNAM-1 protein.

Genes coding for the heavy chains of the antibodies and genes coding for the light chains of the antibodies obtained from the hybridoma line established in the usual manner were cloned, and the amino acid sequences of the heavy and light chains of the antibodies were identified. FIG. 1 is a diagram illustrating the alignment of the amino acid sequences of the heavy chains of anti-human DNAM-1 monoclonal antibody Nos. 1 to 6. CDR1 to 3 are underlined in FIG. 1. FIG. 2 is a diagram illustrating the alignment of the amino acid sequences of the light chains of anti-human DNAM-1 monoclonal antibody Nos. 1 to 6. CDR1 to 3 are underlined in FIG. 2. Table 1 summarizes the correspondence between the amino acid sequences of the heavy and light chains of each of the monoclonal antibodies and the SEQ ID NOs shown in the sequence listing.

TABLE 1

| Antibody | Full length of heavy-chain variable region | Full length of light-chain variable region |
| --- | --- | --- |
| No. 1 | SEQ ID NO: 7 | SEQ ID NO: 8 |
| No. 2 | SEQ ID NO: 9 | SEQ ID NO: 10 |
| No. 3 | SEQ ID NO: 11 | SEQ ID NO: 12 |
| No. 4 | SEQ ID NO: 13 | SEQ ID NO: 14 |
| No. 5 | SEQ ID NO: 15 | SEQ ID NO: 16 |
| No. 6 | SEQ ID NO: 17 | SEQ ID NO: 18 |

Test Example 2

(Study 1 of Reactivity of Anti-human DNAM-1 Monoclonal Antibody)

The reactivities of the monoclonal antibody Nos. 1 and 2 prepared in Test example 1 were determined. Specifically, a BW5147 cell line (hereinafter, may be referred to as "BW"), which is derived from mouse lymphocytes, and a BW5147 cell line in which human DMAM-1 protein was expressed (hereinafter, this BW5147 cell line may be referred to as "DNAM-1/BW") were reacted with the monoclonal antibody No. 1 or 2, and an analysis was made by flow cytometry using a control IgG1 antibody as a reference. With $1 \times 10^5$ cells of each cell line, 30 ng of the antibody was reacted. The reaction of the antibody was made on ice for 30 minutes.

FIG. 3(a) is a graph illustrating the results obtained when the BW cells were reacted with the monoclonal antibody No. 1. FIG. 3(b) is a graph illustrating the results obtained when the DNAM-1/BW cells were reacted with the monoclonal antibody No. 1. FIG. 3(c) is a graph illustrating the results obtained when the BW cells were reacted with the monoclonal antibody No. 2. FIG. 3(d) is a graph illustrating the results obtained when the DNAM-1/BW cells were reacted with the monoclonal antibody No. 2.

The above results showed that both of the monoclonal antibody Nos. 1 and 2 specifically recognized the DNAM-1 protein expressed by the BW cells.

Test Example 3

(Study 2 of Reactivity of Anti-human DNAM-1 Monoclonal Antibody)

The reactivities of the monoclonal antibody Nos. 1 and 2 prepared in Test example 1 with DNAM-1 protein present on the surfaces of human peripheral blood lymphocytes were determined.

The reactivities of the monoclonal antibody Nos. 1 and 2 with $CD3^+$ $CD4^+$ cells ($CD4^+$ T cells), $CD3^+$ $CD8^+$ cells ($CD8^+$ T cells), $CD3^-$ $CD19^+$ cells (B cells), $CD3^-$ $CD56^+$ cells (NK cells), $CD3^+$ $CD56^-$ cells (NKT cells), and $CD14^+$ cells (monocytes) present in the human peripheral blood lymphocytes were determined. Control IgG1 antibody was used as a reference. With $1 \times 10^5$ peripheral blood lymphocytes, 100 ng of the monoclonal antibody No. 1 or 2 was reacted. The reaction of the antibody was made on ice for 30 minutes.

Figure 4:
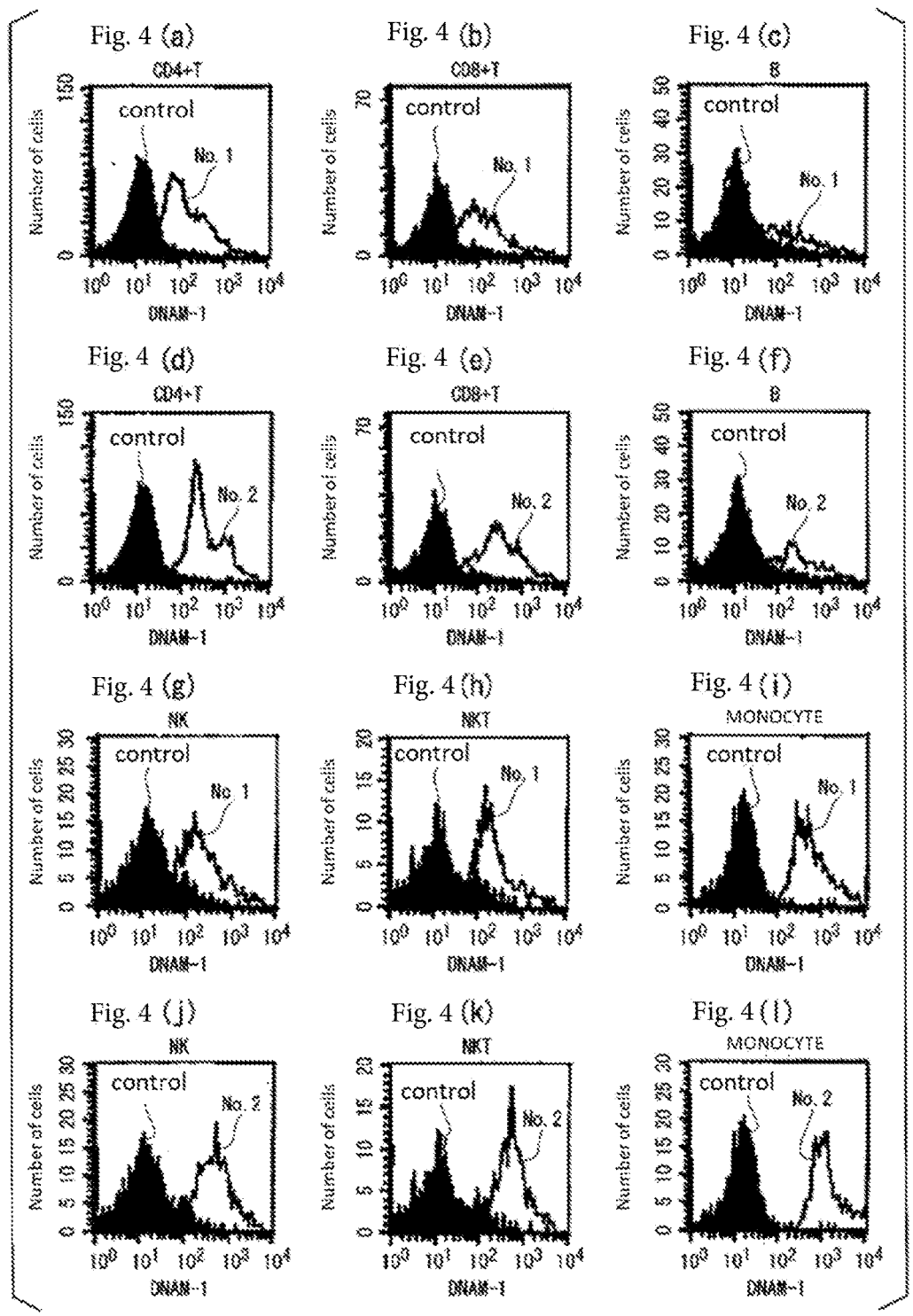
FIGS. 4(a) to 4(l) are graphs illustrating the results obtained in Test example 3.

FIG. 4(a) illustrates the reactivity of the monoclonal antibody No. 1 with the $CD4^+$ T cells. FIG. 4(b) illustrates the reactivity of the monoclonal antibody No. 1 with the $CD8^+$ T cells. FIG. 4(c) illustrates the reactivity of the monoclonal antibody No. 1 with the B cells. FIG. 4(d) illustrates the reactivity of the monoclonal antibody No. 2 with the $CD4^+$ T cells. FIG. 4(e) illustrates the reactivity of the monoclonal antibody No. 2 with the $CD8^+$ T cells. FIG. 4(f) illustrates the reactivity of the monoclonal antibody No. 2 with the B cells. FIG. 4(g) illustrates the reactivity of the monoclonal antibody No. 1 with the NK cells. FIG. 4(h) illustrates the reactivity of the monoclonal antibody No. 1 with the NKT cells. FIG. 4(i) illustrates the reactivity of the monoclonal antibody No. 1 with the monocytes. FIG. 4(j) illustrates the reactivity of the monoclonal antibody No. 2 with the NK cells. FIG. 4(k) illustrates the reactivity of the monoclonal antibody No. 2 with the NKT cells. FIG. 4(l) illustrates the reactivity of the monoclonal antibody No. 2 with the monocytes.

The above results showed that both of the monoclonal antibody No. 1 and No. 2 had reactivity with DNAM-1 protein present on the surfaces of the CD4+ T cells, the CD8+ T cells, the B cells, the NK cells, the NKT cells, and the monocytes.

Test Example 4

(Study 3 of Reactivity of Anti-human DNAM-1 Monoclonal Antibody)

A competitive assay was performed using the monoclonal antibody No. 1 to No. 6 prepared in Test example 1. Specifically, the DNAM-1/BW cells ($1 \times 10^5$ cells) were reacted with 100 ng of the monoclonal antibody No. 2 (pretreatment). Subsequently, the DNAM-1/BW cells were reacted with a specific one of the monoclonal antibody Nos. 1 and 3 to 6 diluted serially. The reaction of the antibody was made on ice for 30 minutes. The reactivities of the antibodies with the DNAM-1/BW cells that had not been subjected to the pretreatment were also determined.

Figure 5:
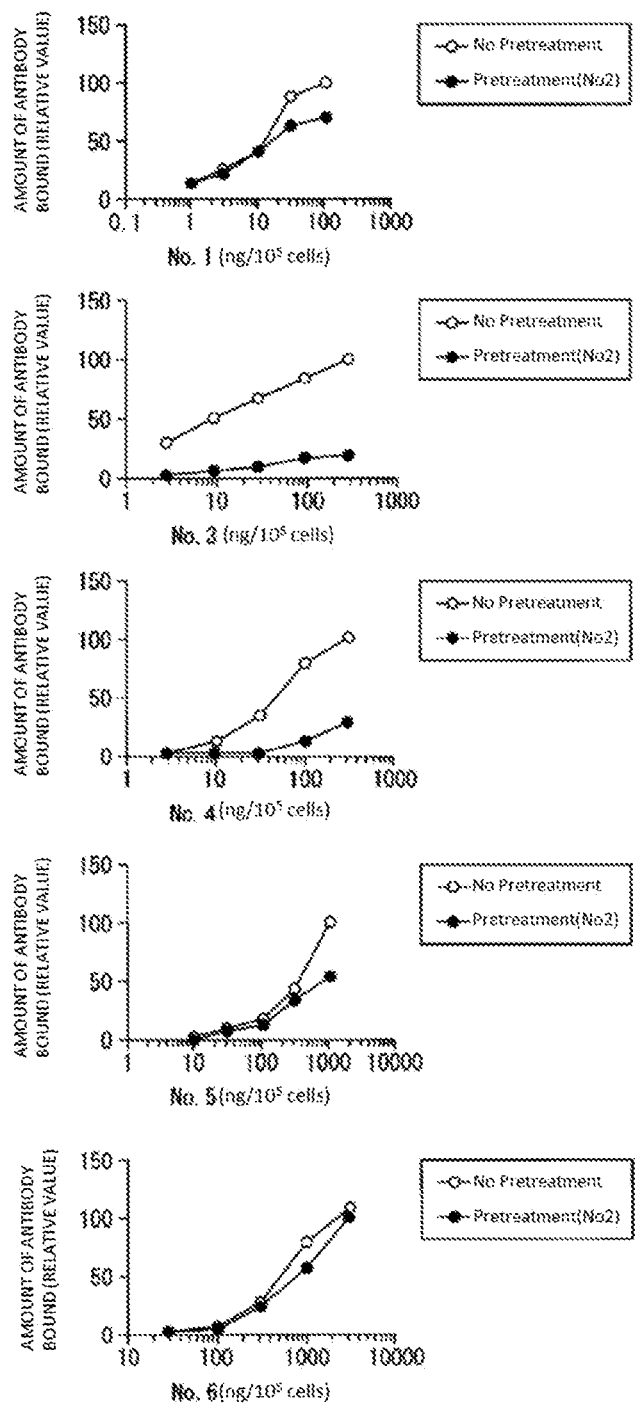
FIGS. 5(a) to 5(e) are graphs illustrating the reactivities of anti-human DNAM-1 monoclonal antibody Nos. 1 to 6 determined in Test example 4.

FIG. 5(a) is a graph illustrating the reactivity of the monoclonal antibody No. 1. FIG. 5(b) is a graph illustrating the reactivity of the monoclonal antibody No. 3. FIG. 5(c) is a graph illustrating the reactivity of the monoclonal antibody No. 4. FIG. 5(d) is a graph illustrating the reactivity of the monoclonal antibody No. 5. FIG. 5(e) is a graph illustrating the reactivity of the monoclonal antibody No. 6.

The result illustrated in FIG. 5(a) was confirmed that the monoclonal antibody No. 1 even had good reactivity with the DNAM-1/BW cells that had been reacted with the monoclonal antibody No. 2. This proves that the monoclonal antibody No. 1 had higher reactivity with the DNAM-1 protein than the monoclonal antibody No. 2.

The result illustrated in FIG. 5(b) was confirmed that the monoclonal antibody No. 3 had poor reactivity with the DNAM-1/BW cells that had been reacted with the monoclonal antibody No. 2. This proves that the monoclonal antibody No. 2 had higher reactivity with the DNAM-1 protein than the monoclonal antibody No. 3.

The results illustrated in FIG. 5(c) was confirmed that the monoclonal antibody No. 4 had poor reactivity with the DNAM-1/BW cells that had been reacted with the monoclonal antibody No. 2. This proves that the monoclonal antibody No. 2 had higher reactivity with the DNAM-1 protein than the monoclonal antibody No. 4.

The result illustrated in FIG. 5(d) was confirmed that the monoclonal antibody No. 5 had reactivity with the DNAM-1/BW cells that had been reacted with the monoclonal antibody No. 2. Taking into account also the results obtained in Test example 5 below, it is considered that the epitopes of the monoclonal antibody No. 5 and No. 2 did not compete with each other.

The result illustrated in FIG. 5(e) is similar to that in FIG. 5(d). Taking into account also the results obtained in Test example 5 below, it is considered that the epitopes of the monoclonal antibody No. 6 and No. 2 did not compete with each other.

Test Example 5

(Study 4 of Reactivity of Anti-human DNAM-1 Monoclonal Antibody)

A test was conducted as in Test example 4, except that the type of antibody that had been reacted with the DNAM-1/BW cells was changed. Specifically, the DNAM-1/BW cells ($1 \times 10^5$ cells) were reacted with a saturating amount of a specific one of the monoclonal antibody Nos. 1 and 3 to 6 (pretreatment). The amounts of the monoclonal antibody Nos. 1 and 3 to 6 used were 30, 300, 300, 500, and 1000 ng, respectively.

Note that, the minimum amounts of monoclonal antibody Nos. 1 to 6 required for saturating the human DNAM-1 antibody expressed on the surfaces of the $1 \times 10^5$ DNAM-1/BW cells were 30, 50, 100, 100, 300, and 300 ng, respectively. Subsequently, the DNAM-1/BW cells were reacted with each of monoclonal antibody No. 2 diluted serially. The reaction of the antibody was made on ice for 30 minutes. The reactivities of the antibodies with the DNAM-1/BW cells that had not been subjected to the pretreatment were also determined.

Figure 6:
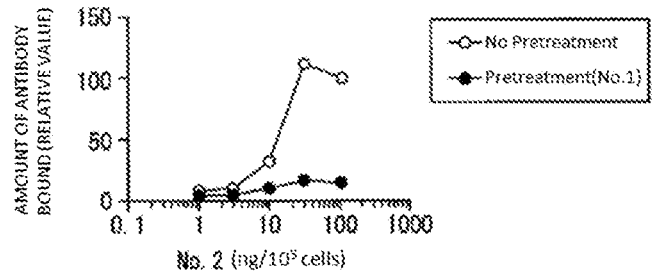
FIGS. 6(a) to 6(e) are graphs illustrating the reactivities of anti-human DNAM-1 monoclonal antibody Nos. 1 to 6 determined in Test example 5.
Figure 6:
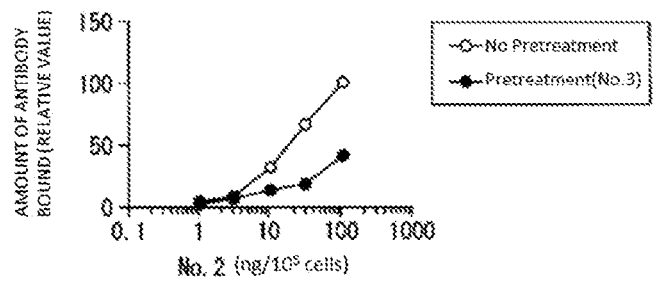
Figure 6:
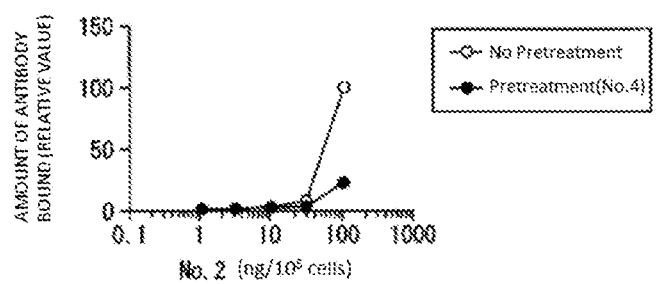
Figure 6:
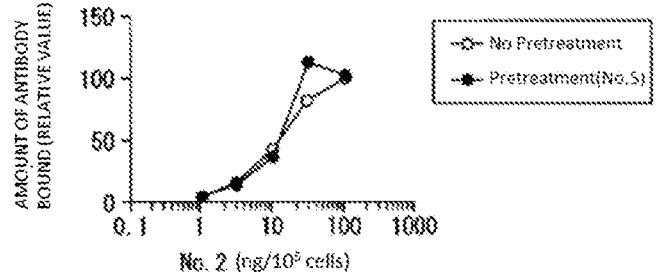
Figure 6:
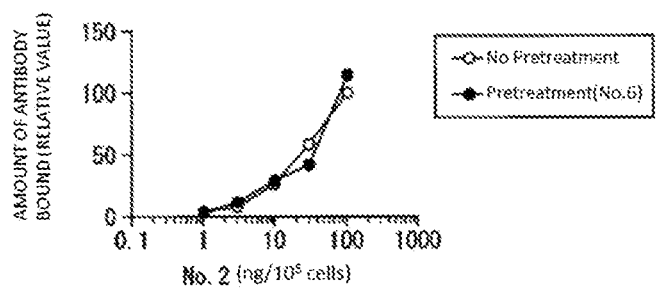

FIG. 6(a) is a graph illustrating the results of the test in which the monoclonal antibody No. 1 was used. FIG. 6(b) is a graph illustrating the results of the test in which the monoclonal antibody No. 3 was used. FIG. 6(c) is a graph illustrating the results of the test in which the monoclonal antibody No. 4 was used. FIG. 6(d) is a graph illustrating the results of the test in which the monoclonal antibody No. 5 was used. FIG. 6(e) is a graph illustrating the results of the test in which the monoclonal antibody No. 6 was used.

The result illustrated in FIG. 6(a) was confirmed that the monoclonal antibody No. 2 had poor reactivity with the DNAM-1/BW cells that had been reacted with the monoclonal antibody No. 1. Taking into account also the results obtained in Test example 4 above, this supports the fact that the monoclonal antibody No. 1 had higher reactivity with the DNAM-1 protein than the monoclonal antibody No. 2.

The result illustrated in FIG. 6(b) was confirmed that the monoclonal antibody No. 2 even had relatively good reactivity with the DNAM-1/BW cells that had been reacted with the monoclonal antibody No. 3. Taking into account also the results obtained in Test example 4 above, this supports the fact that the monoclonal antibody No. 2 had higher reactivity with the DNAM-1 protein than the monoclonal antibody No. 3.

The result illustrated in FIG. 6(c) was confirmed that the monoclonal antibody No. 2 even had relatively good reactivity with the DNAM-1/BW cells that had been reacted with the monoclonal antibody No. 4. Taking into account also the results obtained in Test example 4 above, this supports the fact that the monoclonal antibody No. 2 had higher reactivity with the DNAM-1 protein than the monoclonal antibody No. 4.

The result illustrated in FIG. 6(d) was confirmed that the monoclonal antibody No. 2 had reactivity with the DNAM-1/BW cells that had been reacted with the monoclonal antibody No. 5. Taking into account also the results obtained in Test example 4 above, it is considered that the epitopes of the monoclonal antibody No. 2 and No. 5 did not compete with each other.

The result illustrated in FIG. 6(e) was similar to that in FIG. 6(d). Taking into account also the results obtained in Test example 4 above, it is considered that the epitopes of the monoclonal antibody No. 2 and No. 6 did not compete with each other.

Test Example 6

(Study 5 of Reactivity of Anti-human DNAM-1 Monoclonal Antibody)

It is known that DNAM-1 protein and CD155 protein interact with each other. Accordingly, whether or not the monoclonal antibody No. 1 to No. 6 prepared in Test example 1 are capable of inhibiting the interaction between the DNAM-1 protein and the CD155 protein was determined.

First, a solubilized human CD155 protein was prepared. Specifically, a fusion protein formed by the fusion of human CD155 protein with a human IgG antibody constant region (hereinafter, this fusion protein may be referred to as "hCD155-Fc") was prepared in the conventional manner. The RefSeq ID of the human CD155 protein is NP_001129240.

Then, the DNAM-1/BW cells ($1 \times 10^5$ cells) were reacted with a saturating amount (1000 ng) of the hCD155-Fc protein in advance. Subsequently, the DNAM-1/BW cells were reacted with a specific one of the monoclonal antibody No. 1 to No. 6 diluted serially. The reaction was made on ice for 30 minutes.

FIGS. 7(a) to 7(e) are graphs illustrating the results of the tests in which the monoclonal antibody Nos. 1 and 3 to 6 were used, respectively. The results of the test in which the monoclonal antibody No. 2 was used are also shown in FIGS. 7(a) to 7(e) for comparison.

Figure 7:
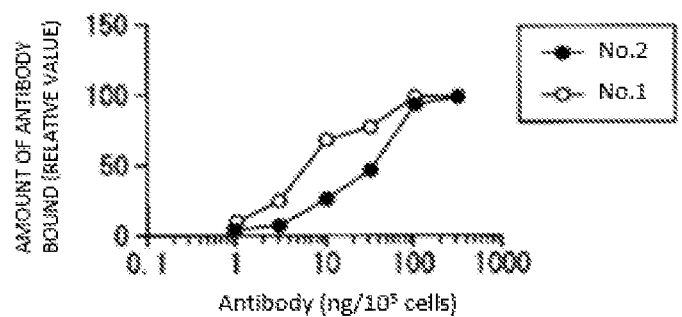
FIGS. 7(a) to 7(e) are graphs illustrating the reactivities of anti-human DNAM-1 monoclonal antibody Nos. 1 to 6 determined in Test example 6.
Figure 7:
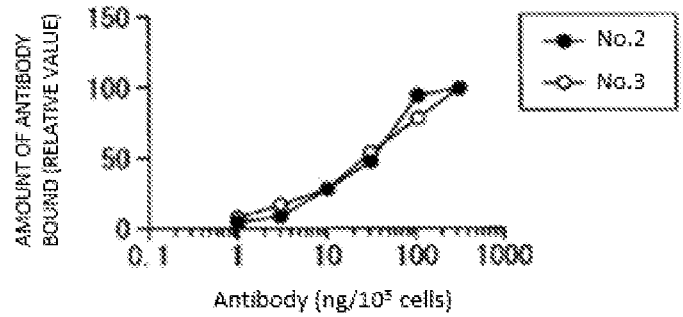
Figure 7:
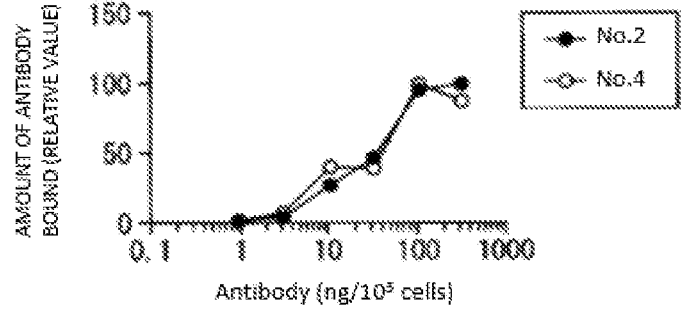
Figure 7:
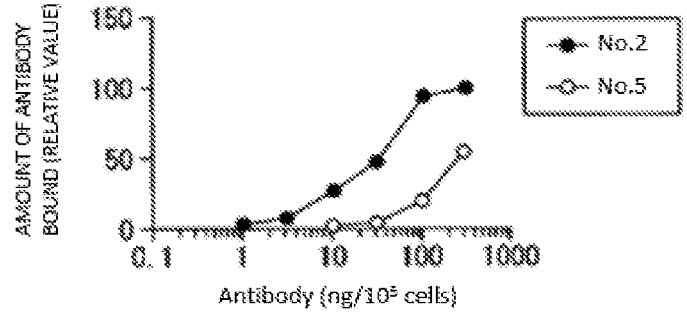
Figure 7:
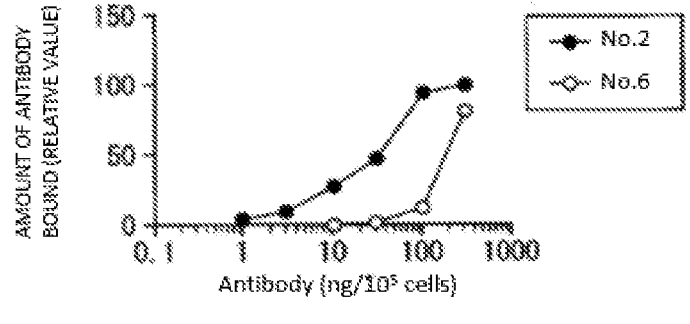

The result illustrated in FIG. 7(a) was confirmed that the monoclonal antibody No. 1 was capable of suitably reacting with the DNAM-1/BW cells that had been reacted with the hCD155-Fc protein and the reactivity was higher than that of the monoclonal antibody No. 2.

The result illustrated in FIG. 7(b) was confirmed that the monoclonal antibody No. 3 was capable of suitably reacting with the DNAM-1/BW cells that had been reacted with the hCD155-Fc protein and the reactivity was comparable to that of the monoclonal antibody No. 2.

The result illustrated in FIG. 7(c) was confirmed that the monoclonal antibody No. 4 was capable of suitably reacting with the DNAM-1/BW cells that had been reacted with the hCD155-Fc protein and the reactivity was comparable to that of the monoclonal antibody No. 2.

The result illustrated in FIG. 7(d) was confirmed that the monoclonal antibody No. 5 was capable of reacting with the DNAM-1/BW cells that had been reacted with the hCD155-Fc protein, but the reactivity was lower than that of the monoclonal antibody No. 2.

The results illustrated in FIG. 7(e) confirmed that the monoclonal antibody No. 6 was capable of reacting with the DNAM-1/BW cells that had been reacted with the hCD155-Fc protein, but the reactivity was lower than that of the monoclonal antibody No. 2.

Test Example 7

(Study 6 of Reactivity of Anti-human DNAM-1 Monoclonal Antibody)

After DNAM-1/BW cells reacted with the hCD155-Fc protein in advance had been reacted with a specific one of the monoclonal antibody No. 1 to No. 6 diluted serially in Test example 6, the hCD155-Fc protein bound to the DNAM-1 protein present on the surfaces of the DNAM-1/BW cells was detected. The detection of the hCD155-Fc protein was conducted using an anti-human IgG antibody. The reaction was made on ice for 30 minutes.

FIGS. 8(a) to 8(e) are graphs illustrating the results of the tests in which the monoclonal antibody Nos. 1 and 3 to 6 were used, respectively. The results of the test in which the monoclonal antibody No. 2 was used are also shown in FIGS. 8(a) to 8(e) for comparison.

Figure 8:
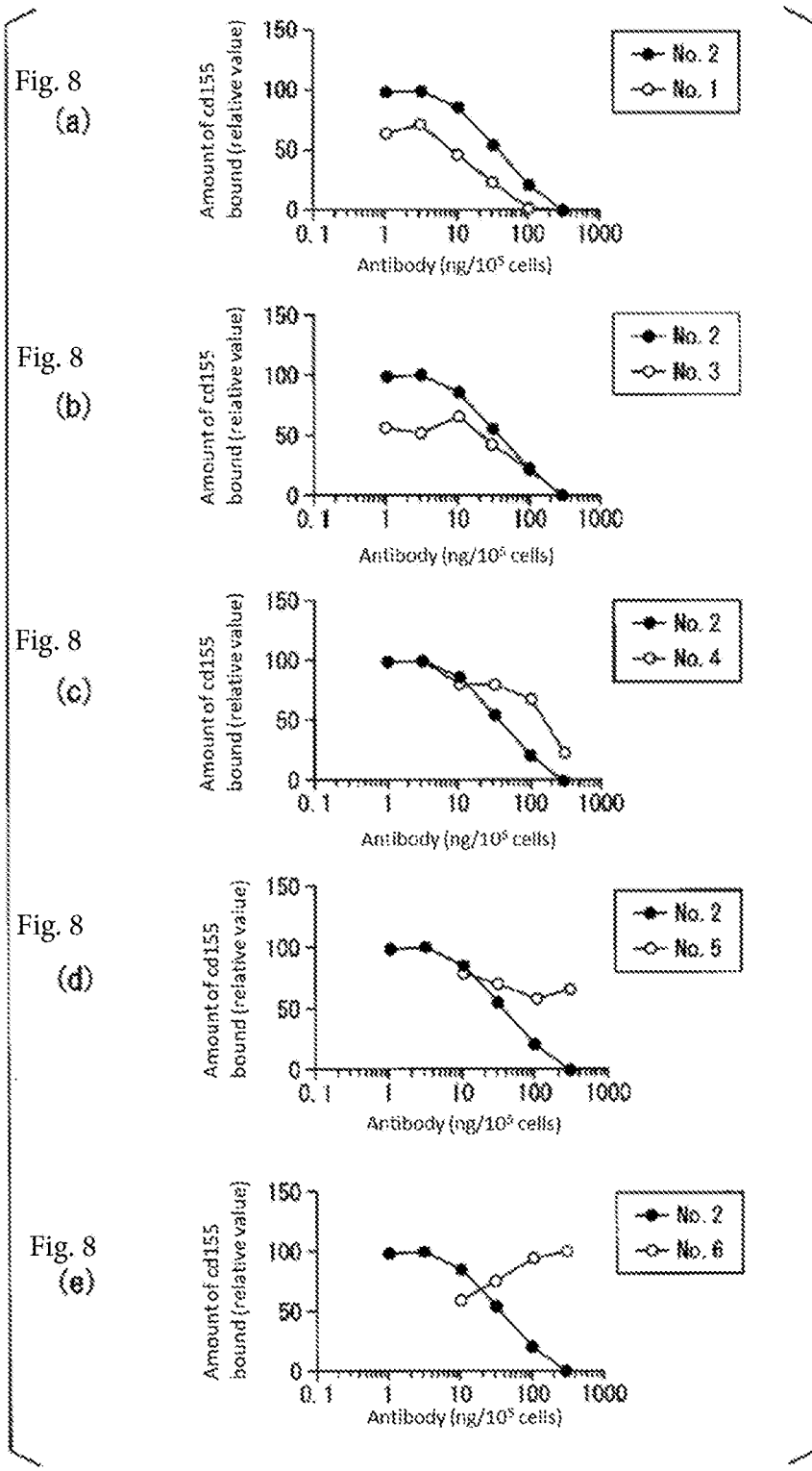
FIGS. 8(a) to 8(e) are graphs illustrating the reactivities of anti-human DNAM-1 monoclonal antibody Nos. 1 to 6 determined in Test example 7.

The result illustrated in FIG. 8(a) was confirmed that the residues of hCD155-Fc protein that after the DNAM-1/BW cells had been reacted with the monoclonal antibody No. 1 decreased in a manner dependent on the concentration of the monoclonal antibody No. 1.

It was also confirmed that the amount of hCD155-Fc protein was substantially zero in the range where the concentration of the monoclonal antibody reacted was high. This proves that both of the monoclonal antibody No. 1 and No. 2 were capable of completely inhibiting the interaction between the DNAM-1 protein and the CD155 protein. The amount of monoclonal antibody No. 1 required for completely inhibiting the interaction between the DNAM-1 protein and the CD155 protein was smaller than that of the amount of monoclonal antibody No. 2 required for completely inhibiting the interaction between the DNAM-1 protein and the CD155 protein. Specifically, the amounts of monoclonal antibody No. 1 and No. 2 required for completely inhibiting the interaction between the DNAM-1 protein and the CD155 protein were 100 and 300 ng, respectively.

The result illustrated in FIG. 8(b) was confirmed that the residues of hCD155-Fc protein after the DNAM-1/BW cells had been reacted with the monoclonal antibody No. 3 decreased in a manner dependent on the concentration of the monoclonal antibody No. 3.

It was also confirmed that, in the range where the concentration of the monoclonal antibody reacted with the DNAM-1/BW cells was low, the reidues of hCD155-Fc protein after the DNAM-1/BW cells had been reacted with the monoclonal antibody No. 3 was smaller than that of hCD155-Fc protein after the DNAM-1/BW cells had been reacted with the monoclonal antibody No. 2. This proves that, in the range where the concentration of the monoclonal antibody reacted with the DNAM-1/BW cells was low, the monoclonal antibody No. 3 had higher activity of inhibiting the interaction between the DNAM-1 protein and the CD155 protein than the monoclonal antibody No. 2. In the range where the concentration of the monoclonal antibody reacted with the DNAM-1/BW cells was high, the difference in the above reactivity between the monoclonal antibody Nos. 2 and 3 was small. The amount of monoclonal antibody No. 3 required for completely inhibiting the interaction between the DNAM-1 protein and the CD155 protein was 300 ng.

The result illustrated in FIG. 8(c) was confirmed that the residues of hCD155-Fc protein after the DNAM-1/BW cells had been reacted with the monoclonal antibody No. 4 decreased in a manner dependent on the concentration of the monoclonal antibody No. 4.

It was also confirmed that the residues hCD155-Fc protein after the DNAM-1/BW cells had been reacted with the monoclonal antibody No. 4 was larger than the that of hCD155-Fc protein after the DNAM-1/BW cells had been reacted with the monoclonal antibody No. 2. This proves that the monoclonal antibody No. 2 had higher activity of inhibiting the interaction between the DNAM-1 protein and the CD155 protein than the monoclonal antibody No. 4. The amount of monoclonal antibody No. 4 required for completely inhibiting the interaction between the DNAM-1 protein and the CD155 protein was 1000 ng.

The result illustrated in FIG. 8(d) was confirmed that the amount of hCD155-Fc protein did not decrease sufficiently even after the DNAM-1/BW cells had been reacted with the monoclonal antibody No. 5. This proves that the monoclonal antibody No. 5 had low activity of inhibiting the interaction between the DNAM-1 protein and the CD155 protein. It was not possible to completely inhibit the interaction between the DNAM-1 protein and the CD155 protein even when 3000 ng of the monoclonal antibody No. 5 was used.

The result illustrated in FIG. 8(e) was confirmed that the amount of hCD155-Fc protein did not decrease sufficiently even after the DNAM-1/BW cells had been reacted with the monoclonal antibody No. 6. This proves that the monoclonal antibody No. 6 had low activity of inhibiting the interaction between the DNAM-1 protein and the CD155 protein. It was not possible to completely inhibit the interaction between the DNAM-1 protein and the CD155 protein even when 3000 ng of the monoclonal antibody No. 6 was used.

Test Example 8

(Function Analysis 1 of Anti-human DNAM-1 Monoclonal Antibody)

A mixed lymphocyte reaction (MLR) assay was conducted in the presence of the monoclonal antibody No. 1 or No. 2 prepared in Test example 1 in order to determine the impacts of the monoclonal antibody on the proliferation of T cells.

An MLR assay measures the proliferation of T cells which occurs when allogeneic stimulating cells are mixed with T cells. Specifically, first, the CD14$^+$ cells ($5\times10^5$ cells) were sampled from human peripheral blood lymphocytes and cultured for 1 week in the presence of interleukin(IL)-4 (40 ng/well) and GM-CSF (50 ng/well) in order to induce dendritic cells. The culture of the CD14$^+$ cells was conducted using a 24-well plate. CD8$^+$ T cells were sampled from the human peripheral blood lymphocytes derived from another donor.

The CD8$^+$ T cells were reacted with a certain amount (1 μg/mL) of the F(ab')$_2$ monoclonal antibody No. 1, the F(ab')$_2$ monoclonal antibody No. 2, or the F(ab')$_2$ control IgG (reference) which was equal to or larger than the saturating amount. Subsequently, the CD8$^+$ T cells were co-cultured with the dendritic cells. The number of the CD8$^+$ T cells was $5\times10^4$. The number of the dendritic cells was $5\times10^3$.

At 48 hours after the cocultivation was started, the above antibody was again added in an amount of 1 μg/mL. At 72 hours after the cocultivation was started, bromodeoxyuridine (BrdU) was added. At 96 hours after the cocultivation was started, staining was performed using an anti-BrdU antibody in order to measure the proliferation of the CD8$^+$ T cells.

Figure 9:
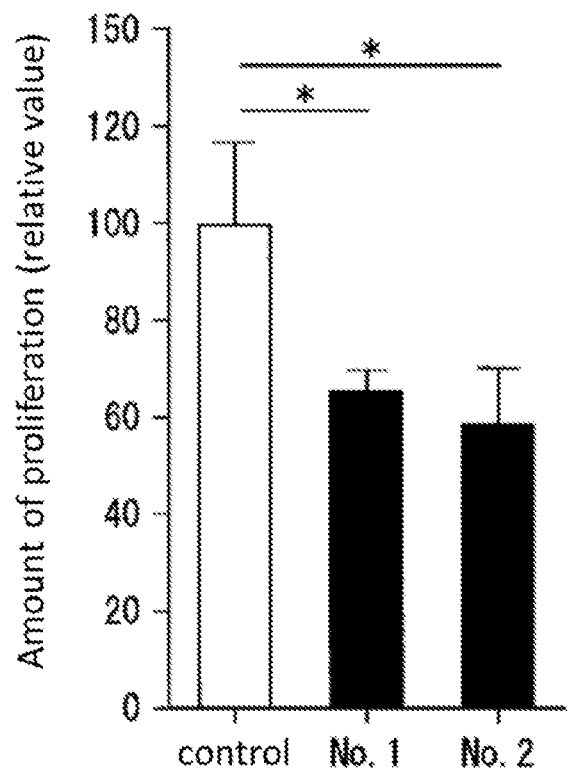
FIG. 9 is a graph illustrating the results of a mixed lymphocyte reaction assay conducted in Test example 8.

FIG. 9 is a graph illustrating the results of the MLR assay. In FIG. 9, the symbol "★" denotes that there was a significant difference therebetween with a significance level of less than 5%. It was confirmed that the proliferation of the CD8$^+$ T cells was significantly limited even when any one of the monoclonal antibody No. 1 and No. 2 was added. The above results show that the monoclonal antibody No. 1 and No. 2 can affect the functions of the human T cells.

Test Example 9

(Functions Analysis 2 of Anti-human DNAM-1 Monoclonal Antibody)

The functions of the monoclonal antibody No. 1 prepared in Test example 1 were analyzed using a mouse model of graft-versus-host disease.

The mouse model of graft-versus-host disease used in the Test example 9 was a model in which hCD155Tg/NOG mice generated by crossing a NOG mouse (NOD/Shi-scid, IL-2 Rynull mouse), which is an immunodeficient mouse, with a human CD155 transgenic mouse were exposed to radiation, human peripheral blood lymphocytes were subsequently transplanted into the mice, and the symptoms of graft-versus-host disease were determined on the basis of weight change and survival rate.

Figure 10:
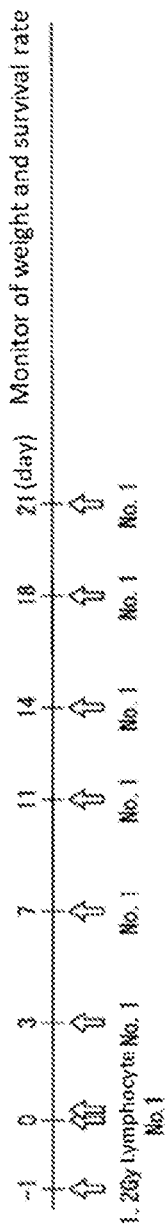
FIG. 10 is a diagram illustrating the experiment protocol in Test example 9.

FIG. 10 is a diagram illustrating the experiment protocol of the test. On the day before the initiation of the test, the hCD155Tg/NOG mice (female, 8 weeks old) were exposed to 1.2 Gy radiation. On the starting day of the test, $2.5\times10^6$ cells/mouse of human peripheral blood lymphocytes were transplanted into the mice by tail vein injection. Subsequently, 300 μg/0.2 mL of the F(ab')$_2$ monoclonal antibody No. 1 was administered intraperitoneally to the mice (n=6). Mice to which a phosphate buffer solution (PBS) was administered instead of the antibody were used as a reference (n=6). Changes in the weights of the mice and the survival rates of the mice were measured in order to determine the symptoms of graft-versus-host disease. The antibody was administered intraperitoneally to the mice in the same amount as described above on the 3rd, 7th, 11th, 14th, 18th, and 21st days after the initiation of the test.

Figure 11:
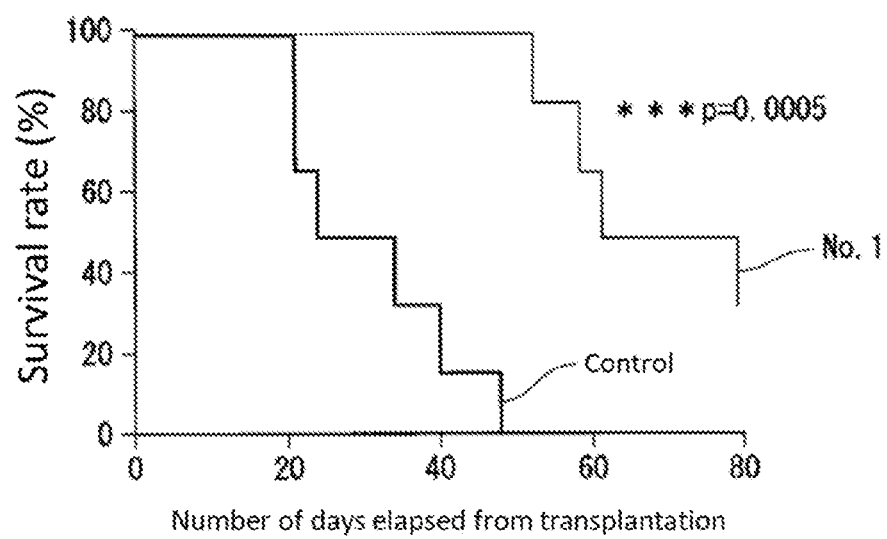
FIG. 11 is a graph illustrating the survival rates of mice determined in Test example 9.

FIG. 11 is a graph illustrating the survival rates of the mice. The survival rate of the mice to which the monoclonal antibody No. 1 was administered was significantly increased. This proves that the administration of the monoclonal antibody No. 1 may prevent graft-versus-host disease.

The deterioration in liver function in the mice was determined by measuring the glutamic pyruvic transaminase (ALT) activity and the glutamic oxaloacetic transaminase (AST) activity in the blood. Increases in the ALT and AST activities in the blood indicate impairments of liver function.

Figure 12:
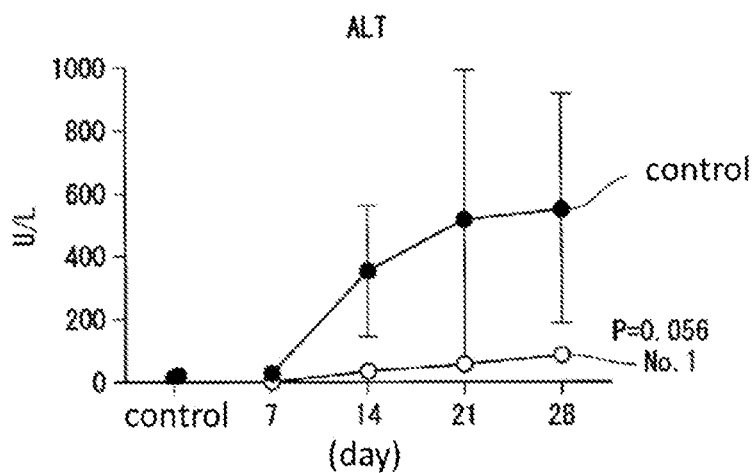
FIGS. 12(a) and 12(b) are graphs illustrating the liver functions of mice determined in Test example 9.
Figure 12:
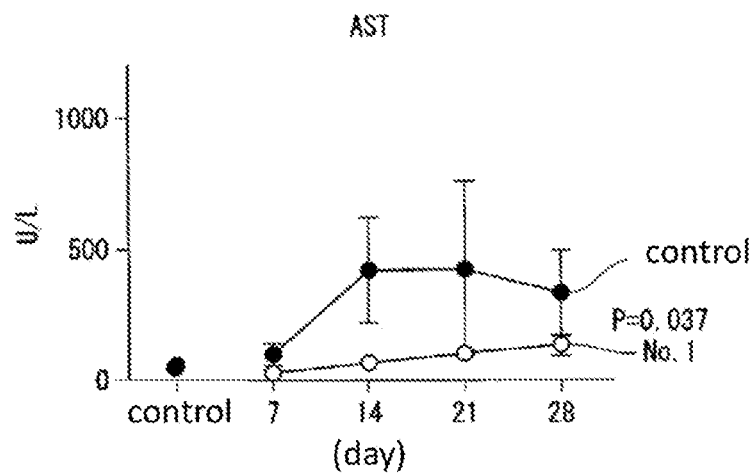

FIG. 12(a) is a graph illustrating the result of ALT activity measured. FIG. 12(b) is a graph illustrating the result of AST activity measured. It was confirmed that the deterioration in liver function in the mice to which the monoclonal antibody No. 1 was administered was suppressed.

Test Example 10

(Functions Analysis 3 of Anti-human DNAM-1 Monoclonal Antibody)

The functions of the monoclonal antibody No. 1 prepared in Test example 1 were analyzed using the same mouse model of graft-versus-host disease as in Test example 9, except that the experiment protocol was changed from Test example 9. The effect of the monoclonal antibody No. 1 on the treatment of graft-versus-host disease was determined.

Figure 13:
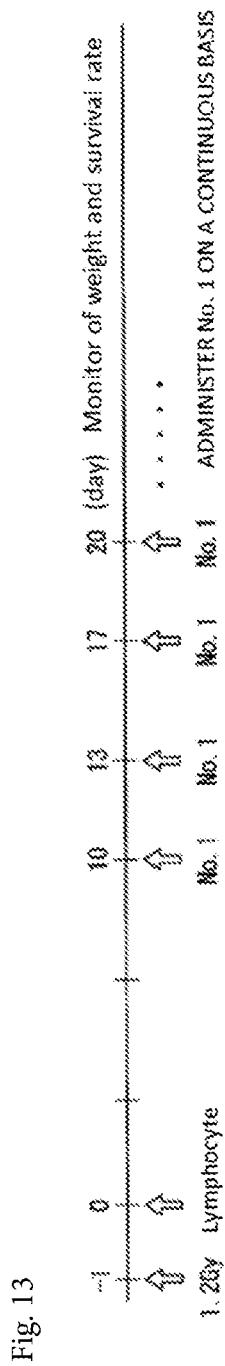
FIG. 13 is a diagram illustrating the experiment protocol in Test example 10.

FIG. 13 is a diagram illustrating the experiment protocol of the test. On the day before the initiation of the test, the hCD155Tg/NOG mice (female, 8 weeks old) were exposed to 1.2 Gy radiation. On the starting day of the test, $2.5\times10^6$ cells/mouse of human peripheral blood lymphocytes were transplanted into the mice by tail vein injection. Subsequently, changes in the weights of the mice and the survival rates of the mice were measured in order to determine the symptoms of graft-versus-host disease. On the 10th, 13th, 17th, and 20th days after the initiation of the test, 300 μg/0.2 mL of the F(ab')$_2$ monoclonal antibody No. 1 was administered intraperitoneally to the mice. The monoclonal antibody No. 1 was administered to each of the mice twice a week on a continuous basis until the mouse died. Mice to which a PBS was administrated instead of the antibody were used as a reference.

Figure 14:
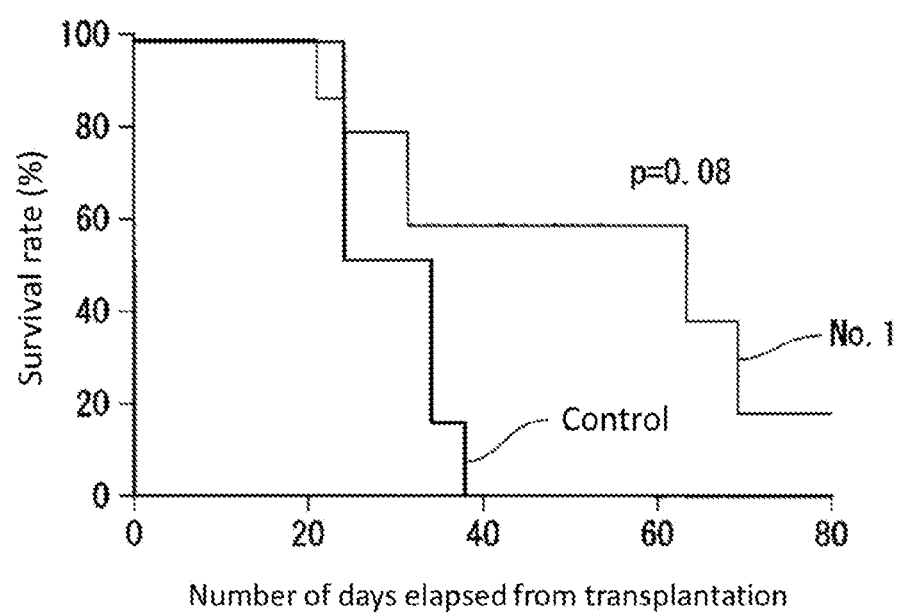
FIG. 14 is a graph illustrating the survival rates of mice determined in Test example 10.

FIG. 14 is a graph illustrating the survival rates of the mice. As result, the survival rate of the mice to which the monoclonal antibody No. 1 was administered was significantly increased. This proves that the administration of the monoclonal antibody No. 1 may treat graft-versus-host disease.

Test Example 11

(Functions Analysis 4 of Anti-human DNAM-1 Monoclonal Antibody)

A comparison was made between the functions of the monoclonal antibody No. 1 and No. 2 prepared in Test example 1. Specifically, CD8$^+$ T cells were separated from human peripheral blood monocytes and cultured in the presence of anti-CD3 antibody (catalog No. 555336, produced by BD Bioscience, 0.25 µg/mL), the anti-CD28 antibody (catalog No. 555725, produced by BD Bioscience, 1 µg/mL), and IL-2 (catalog No. 554603, produced by BD Bioscience, 0.02 µg/mL) for 7 days so as to be activated.

Then, to the activated CD8$^+$ T cells, control IgG1 antibody (reference), the monoclonal antibody No. 1, or the monoclonal antibody No. 2 was added at a proportion of 10 mg/10$^6$ cells in order to bind the antibody to the activated CD8$^+$ T cells by incubation at 4° C. for 30 minutes.

Subsequently, the CD8$^+$ T cells treated with the antibody were mixed with hCD155-expressed cells, which served as target cells, at a ratio of CD8$^+$ T cell:hCD155-expressed cell=1:5. Then, co-cultivation was performed at 37° C. for 4 hours. The hCD155-expressed cells used were BW5147 cells on which hCD155 had been forcibly expressed.

The cytotoxic activity of each of the sets of CD8$^+$ T cells was determined. The cytotoxic activity of CD8$^+$ T cells was determined on the basis of the expression of CD107a on the CD8$^+$ T cells. CD107a is a marker of degranulation of CD8$^-$ T cells.

Figure 15:
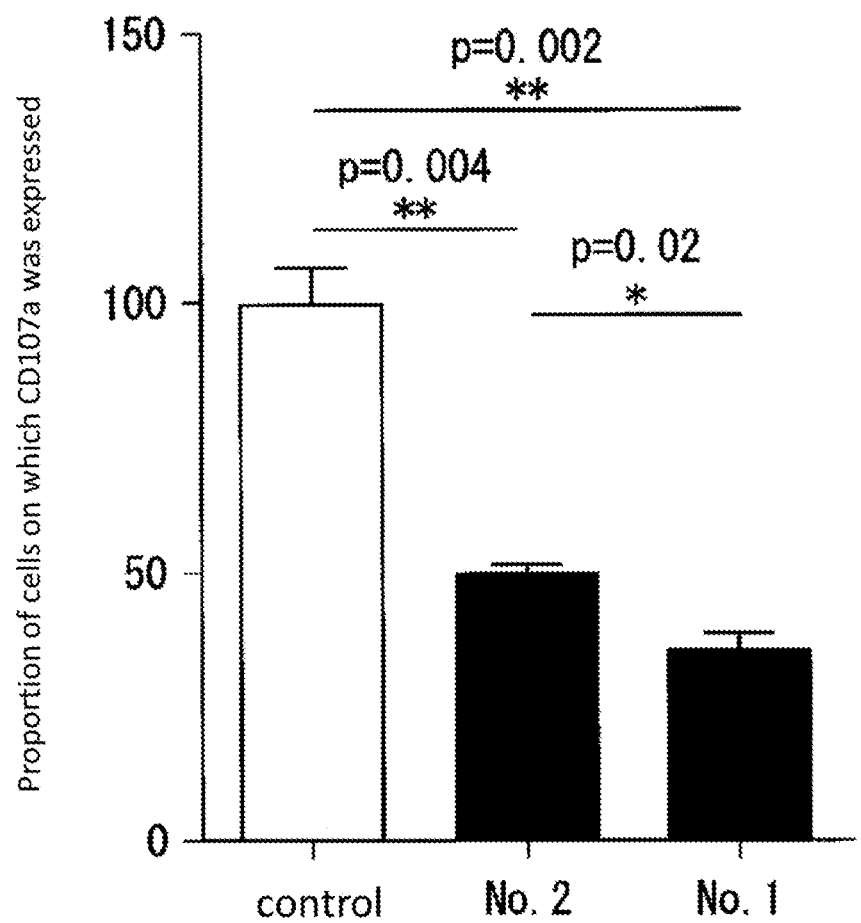
FIG. 15 is a graph illustrating the cytotoxic activities of $CD8^+$ T cells reacted with anti-human DNAM-1 monoclonal antibodies determined in Test example 11.

FIG. 15 is a graph illustrating the results of the study. FIG. 15 illustrates the proportion of cells on which CD107a was expressed to the CD8$^+$ T cells treated with a specific one of the monoclonal antibody No. 1 or monoclonal antibody No.2, with 100% being the proportion of cells on which CD107a was expressed to the CD8$^+$ T cells treated with the control IgG1 antibody (reference).

In FIG. 15, "p=0.002" means that there was a significant difference therebetween with a significance level of less than 0.2%; "p=0.004" means that there was a significant difference therebetween with a significance level of less than 0.4%; and "p=0.02" means that there was a significant difference therebetween with a significance level of less than 2%.

As a result, it was confirmed that, when the binding between the DNAM-1 present on the CD8$^+$ T cells and hCD155 present on the target cells was inhibited with the anti-DNAM-1 antibody, the cytotoxic activity of the CD8$^+$ T cells was inhibited. It was also confirmed that the degree of the inhibition of cytotoxic activity achieved using the monoclonal antibody No. 1 was significantly larger than that achieved using the monoclonal antibody No. 2.

Test Example 12

(Study of Regulatory T Cells)

The functions of the monoclonal antibody No. 1 prepared in Test example 1 were analyzed using the same mouse model of graft-versus-host disease as in Test example 9.

Specifically, first, on the day before the initiation of the test, hCD155Tg/NOG mice (female, 8 weeks old) generated by crossing a NOG mouse (NOD/Shi-scid, IL-2 Rynull mouse), which is an immunodeficient mouse, with a human CD155 transgenic mouse were exposed to 1.2 Gy radiation. Then, on the starting day of the test, 2.5×10$^6$ cells/mouse of human peripheral blood lymphocytes were transplanted into the mice by tail vein injection. Subsequently, 300 µg/0.2 mL of the F(ab')$_2$ monoclonal antibody No. 1 was administered intraperitoneally to the mice (n=6). Mice to which a phosphate buffer solution (PBS) was administrated instead of the antibody were used as a reference (n=6). The antibody was administered intraperitoneally to the mice in the same amount as described above on the 3rd, 7th, and 11th days after the initiation of the test.

Subsequently, on the 14th day after the initiation of the test, the spleen and peripheral blood were sampled from each of the mice and analyzed by flow cytometry in order to determine the proportion of the regulatory T cells in the spleen and peripheral blood. The CD4$^+$ Foxp3$^+$ cells were detected as regulatory T cells.

Figure 16:
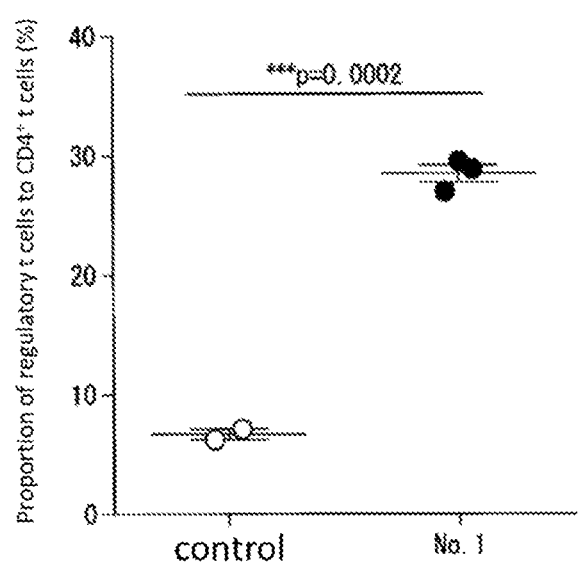
FIG. 16(a) is a graph illustrating the proportions of regulatory T cells to $CD4^+$ T cells in the spleens of mice determined at 14 days after the administration of monoclonal antibody No. 1 in Test example 12.
FIG. 16(b) is a graph illustrating the proportions of regulatory T cells to $CD4^+$ T cells in the peripheral bloods of mice determined at 14 days after the administration of monoclonal antibody No. 1 in Test example 12.
Figure 16:
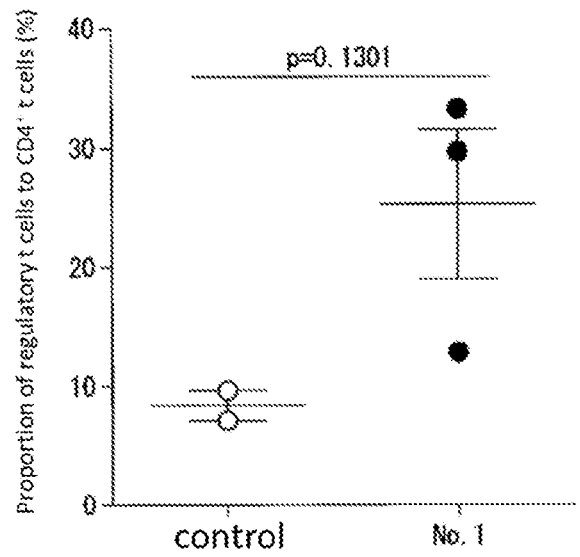

FIG. 16($a$) is a graph illustrating the results of the proportion of the regulatory T cells to the CD4$^+$ T cells in the spleen of each of the mice determined at 14 days after the administration of the monoclonal antibody No. 1. FIG. 16($b$) is a graph illustrating the proportion of the regulatory T cells to the CD4$^+$ T cells in the peripheral blood of each of the mice determined at 14 days after the administration of the monoclonal antibody No. 1.

As a result, it was confirmed that the administration of the monoclonal antibody No. 1 significantly increased the proportion of regulatory T cells.

Test Example 13

(Study of Autoimmune Disease)

The functions of the anti-DNAM-1 antibody were determined using a model of experimental autoimmune encephalomyelitis. Specifically, first, on the day before the initiation of the test, 100 µg/0.2 mL of an anti-mouse DNAM-1 antibody was administered intraperitoneally to the C57BL/6J mice (n=8). C57BL/6J mice to which 100 µg/0.2 mL of a control IgG antibody was administrated intraperitoneally were used as a reference (n=9).

Subsequently, at the initiation of the test, 50 pg/0.2 mL of peptide which is equivalent to the amino acid sequence between 33$^{rd}$ and 55th in Myelin oligodendrocyte glycoprotein (MOG) was administered subcutaneously to the back of each of the mice. Then, 200 ng/0.2 mL of pertussis toxin was administered intraperitoneally to the mice. Furthermore, the 200 ng/0.2 mL of pertussis toxin was administered intraperitoneally to each of the mice also on the second day after the initiation of the test.

Subsequently, on the 1st, 3rd, 7th, 11th, and 13th days after the initiation of the test, 100 µg/0.2 mL of an anti-mouse DNAM-1 antibody or 100 µg/0.2 mL of a control IgG antibody was administered to the mice.

The incidence rate of encephalomyelitis and clinical score were determined by monitoring the mice after the initiation of the test. The clinical score was the average of the scores determined in accordance with the following criteria.

Figure 17:
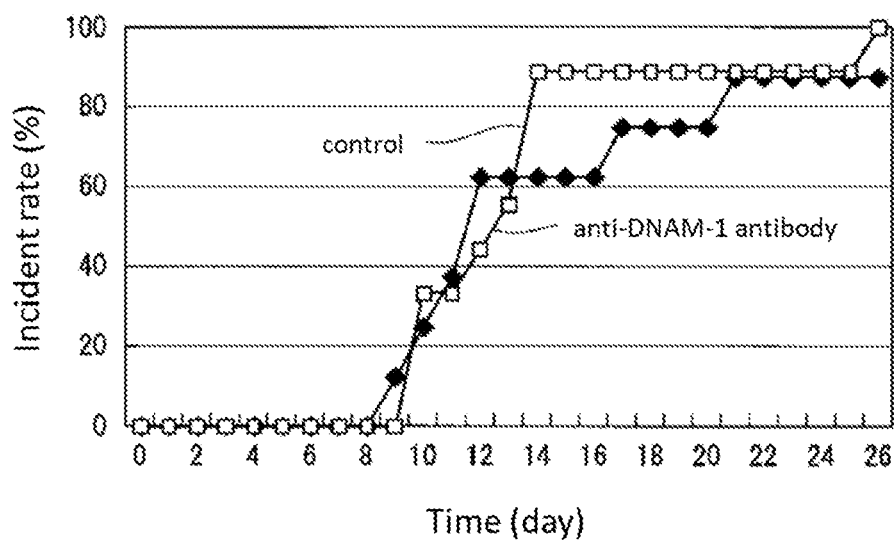
FIG. 17(a) is a graph illustrating the incidence rate of encephalomyelitis determined in Test example 13.
FIG. 17(b) is a graph illustrating the average clinical score calculated in Test example 13.
Figure 17:
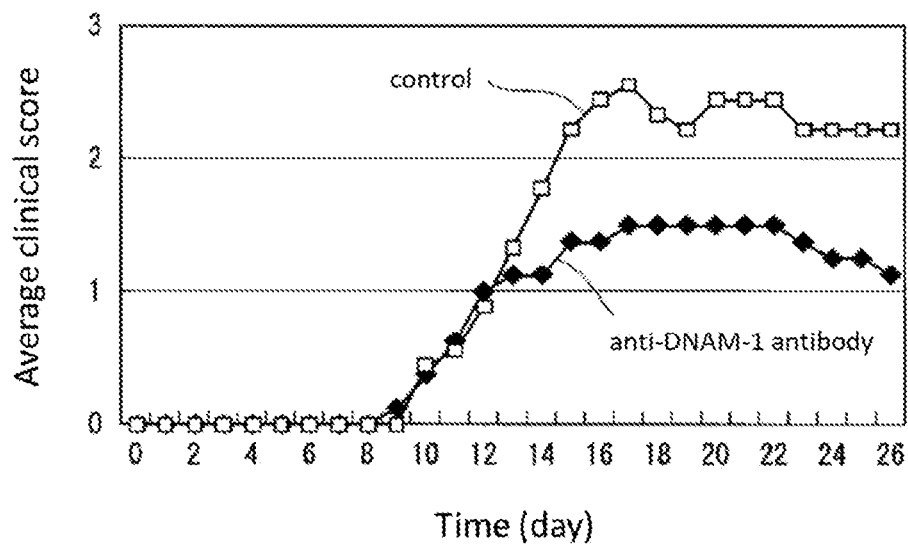

(Clinical Score)
  0: Normal
  1: Tail tonus drop
  2: Completely limp tail
  3: Gait abnormality
  4: Complete weakness of hind paws
  5: Complete weakness of hind paws with forepaw paralysis
  6: Death FIG. 17($a$) is a graph illustrating the result of the incidence rates of encephalomyelitis measured. FIG. 17($b$) is a graph illustrating the result of the average clinical scores calculated. In FIGS. 17(a) and 17(b), the horizontal axis shows the time (day) elapsed from the initiation of the test. As a result, it was confirmed that the administration of the anti-DNAM-1 antibody improved the clinical score of autoimmune encephalomyelitis.

Test Example 14

(Study of Hepatic Fibrosis)

A study of hepatic fibrosis was conducted using DNAM-1 gene knockout (hereinafter, may be referred to as "DNAM-1KO") mice instead of the administration of the anti-DNAM-1 antibody. Wild-type mice were used as a reference. A model of bile duct ligation (BDL) was used in the test.

Specifically, first, the peritoneal cavity of each of the mice was opened and the common bile duct was ligated at the initiation of the test to prepare a BDL model. Then, on the 3rd, 7th, 14th, and 21st days after the initiation of the test, blood was sampled from the orbital sinus of each of the mice. Subsequently, serum was separated from the blood sample obtained, and the amounts of alkaline phosphatase and total bilirubin present in the serum were determined using a clinical chemistry analyzer (Model: "DRI-CHEM", produced by FUJIFILM Holdings Corporation). Note that, alkaline phosphatase and total bilirubin are indices of damages of liver and biliary tract.

On the 21st day after the initiation of the test, the whole body of each of the mice was perfused and the liver was harvested from the mouse. Each of the harvested livers was fixed and embedded into paraffin. Then, tissue slices were prepared. The tissue slices were stained with sirius red and observed with a microscope. Sirius red is a dye that binds to a collagen triple helix.

Figure 18:
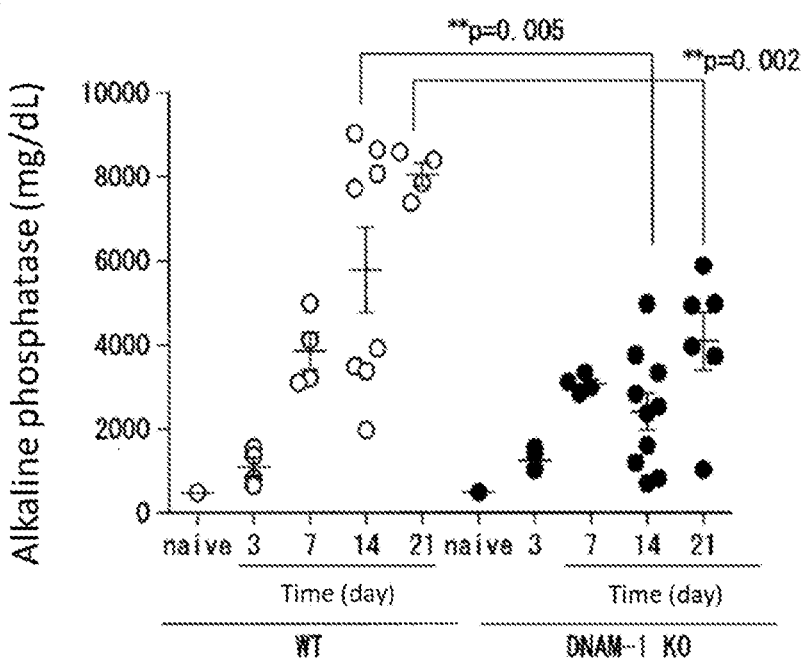
FIG. 18(a) is a graph illustrating the amount of alkaline phosphatase present in serum determined in Test example 14.
FIG. 18(b) is a graph illustrating the amount of total bilirubin present in serum determined in Test example 14.
Figure 18:
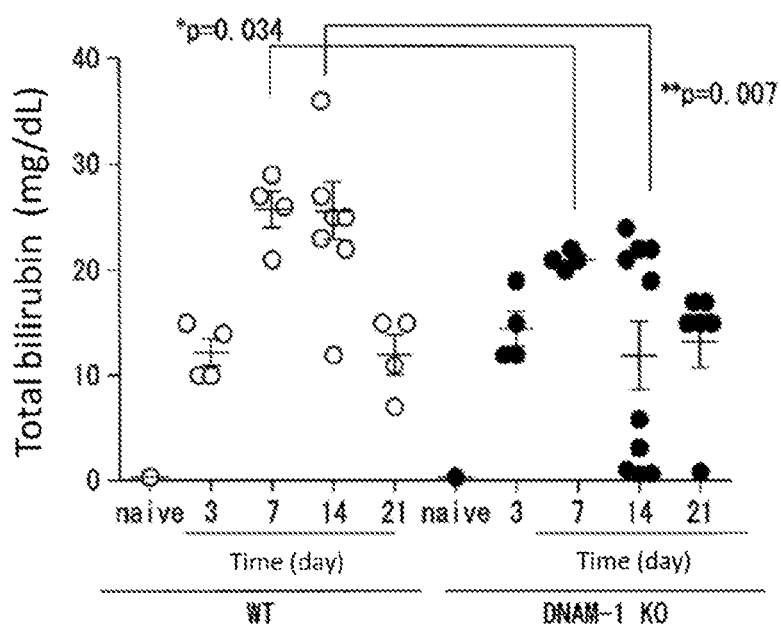

FIG. 18(a) is a graph illustrating the result of the amount of alkaline phosphatase present in the serum quantified. In FIG. 18(a), "WT" denotes the results of the wild-type mice; "DNAM-1 KO" denotes the results of the DNAM-1 knockout mice; and "naive" denotes the results of mice that had not been subjected to the bile duct ligation. The horizontal axis shows the time (day) elapsed from the initiation of the test. As a result, it was confirmed that the amounts of alkaline phosphatase present in the serums of the DNAM-1 knockout mice were significantly smaller than those of the control wild-type mice.

FIG. 18(b) is a graph illustrating the result of the amount of total bilirubin present in the serum quantified. In FIG. 18(b), "WT" denotes the results of the wild-type mice; "DNAM-1 KO" denotes the results of the DNAM-1 knockout mice; and "naive" denotes the results of mice that had not been subjected to the bile duct ligation. The horizontal axis shows the time (day) elapsed from the initiation of the test. As a result, it was confirmed that the amounts of total bilirubin present in the serums of the DNAM-1 knockout mice were significantly smaller than those of the wild-type mice.

Figure 19:
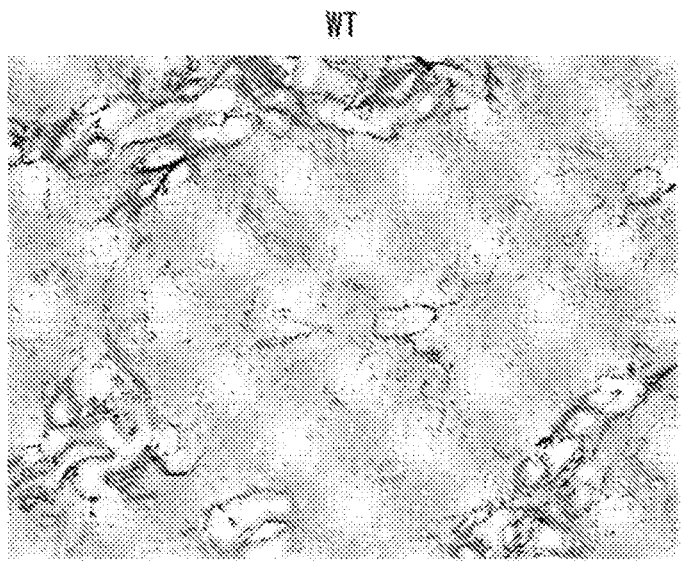
FIG. 19(a) is a micrograph of the liver tissue of a control mouse used in Test example 14.
FIG. 19(b) is a micrograph of the liver tissue of a DNAM-1 knockout mouse used in Test example 14.
Figure 19:
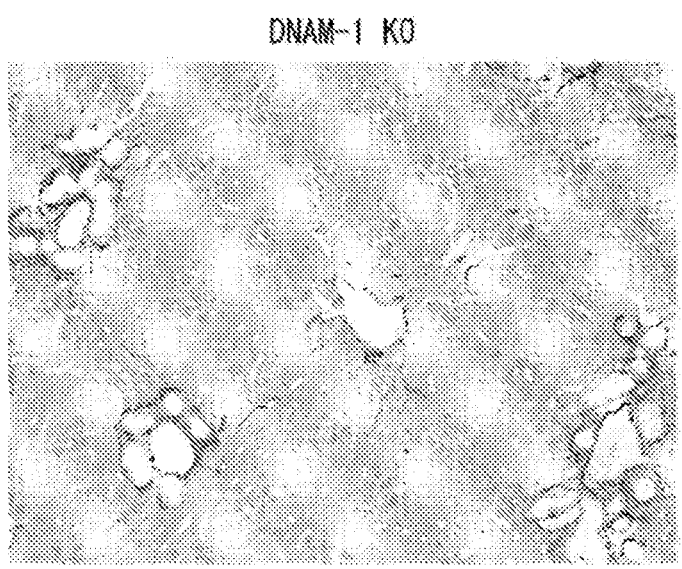

FIGS. 19(a) and 19(b) are micrographs of a liver tissue. FIG. 19(a) is a photograph of the liver tissue of one of the control wild-type mice (WT). FIG. 19(b) is a photograph of the liver tissue of one of the DNAM-1 knockout mice (DNAM-1 KO). Both of the micrographs were taken with a 20-fold magnification. As a result, it was confirmed that hepatic fibrosis was significantly reduced in the DNAM-1 knockout mouse compared with the wild-type mouse.

The above results show that administering the anti-DNAM-1 antibody to a living body may reduce hepatic fibrosis.

Test Example 15

(Study of Renal Fibrosis)

A study of renal fibrosis was conducted using DNAM-1 gene knockout mice instead of the administration of the anti-DNAM-1 antibody. Wild-type mice were used as a reference. A model of unilateral ureteral obstruction (UUO) was used in the test.

Specifically, first, at the initiation of the test, the peritoneal cavity of each of the mice was opened and the right ureter was ligated in order to prepare an UUO model. The left kidney was untreated. Then, on the seventh day after the initiation of the test, the whole body of each of the mice was perfused and both kidneys were harvested from each of the mice. Subsequently, the harvested kidneys were fixed with formalin and embedded into paraffin to prepare the tissue slices. The tissue slices were stained with Masson's trichrome and observed. The kidneys fixed with paraformaldehyde were embedded into an OCT compound to prepare the tissue slices. Then, the tissue slices were immunostained. The area of the α-smooth muscle actin (a-SMA) positive region, which is an index of fibrosis, was calculated.

Figure 20:
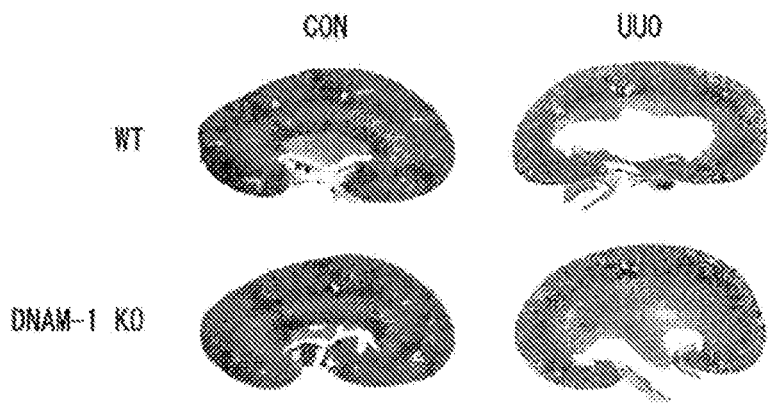
FIG. 20(a) includes photographs of Masson's trichrome-stained sections of kidneys taken in Test example 15.
FIG. 20(b) is a graph illustrating the areas of renal cortices determined based on the results illustrated in FIG. 20(a).
Figure 20:
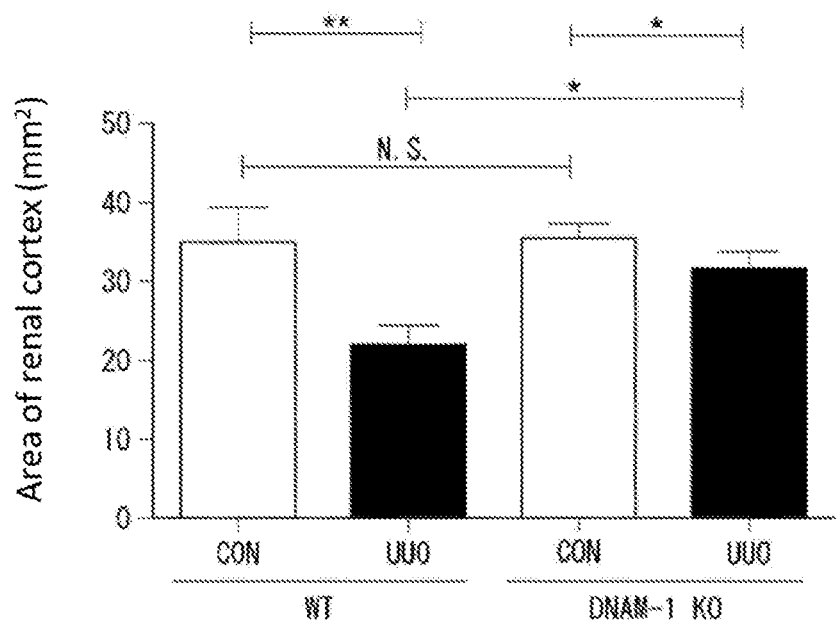

FIG. 20(a) are photographs of sections of kidneys stained with Masson's trichrome. FIG. 20(b) is a graph illustrating the result of the areas of renal cortices determined on the basis of the results illustrated in FIG. 20(a). In FIGS. 20(a) and 20(b), "UUO" denotes the results of the right kidney with the ligated ureter, while "CON" denotes the results of the untreated left kidney; and "WT" denotes the results obtained by the tests in which the wild-type mice were used, while "DNAM-1 KO" denotes the results obtained by the tests in which the DNAM-1 knockout mice were used. In FIG. 20(b), the symbol "*" means that there was a significant difference therebetween with a significance level of less than 5%; the symbol "**" means that there was a significant difference therebetween with a significance level of less than 1%; and "N.S." means that there was no significant difference therebetween. As a result, it was confirmed that the destruction of renal tissue resulting from the ligation of ureter was significantly reduced in the DNAM-1 knockout mice compared with the wild-type mice.

Figure 21:
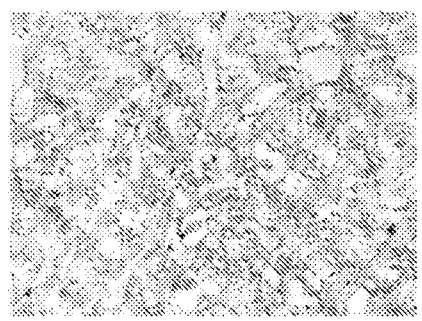
FIG. 21(a) is a micrograph of a typical tissue slice of the kidney of a control mouse immunostained with an anti-α-SMA antibody in Test example 15.
FIG. 21(b) is a micrograph of a typical tissue slice of the kidney of a DNAM-1 knockout mouse immunostained with an anti-α-SMA antibody in Test example 15.
FIG. 21(c) is a graph illustrating the areas of α-SMA positive region in the kidney tissue of mice belonging to each of the groups calculated in Test example 15.
Figure 21:
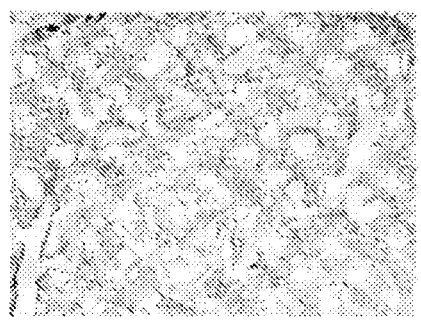
Figure 21:
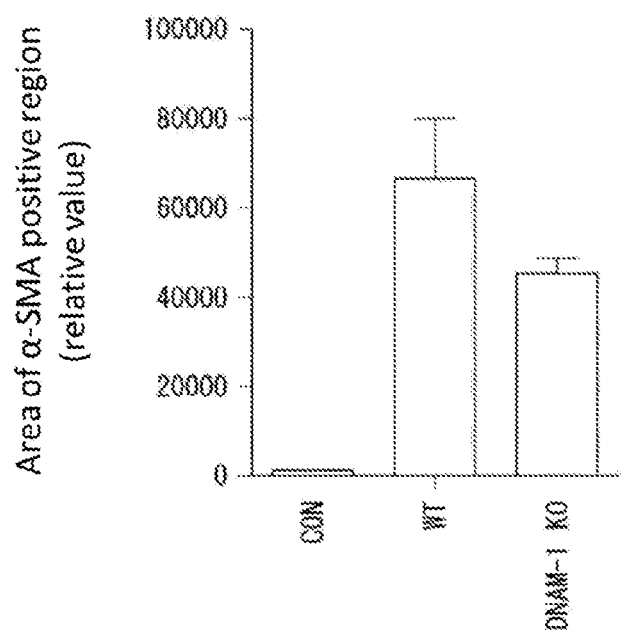

FIGS. 21(a) and 21(b) are micrographs of a renal tissue slice immunostained with anti-α-SMA antibody. FIG. 21(a) illustrates a typical tissue slice of the right kidney with the ligated ureter in the control wild-type mouse, while FIG. 21(b) illustrates a typical tissue slice of the right kidney with the ligated ureter in the DNAM-1 knockout mouse. FIG. 21(c) is a graph illustrating the result of the area of the α-SMA positive region of the renal tissue calculated in each of the mice.

In FIGS. 21(a) to 21(c), "WT" denotes the results obtained by the tests in which the wild-type mice were used, while "DNAM-1 KO" denotes the results obtained by the tests in which the DNAM-1 knockout mice were used. In FIG. 21(c), "CON" denotes the area of the α-SMA positive region in the untreated left kidney. As a result, it was confirmed that the fibrosis of renal tissue resulting from the ligation of ureter was significantly reduced in the DNAM-1 knockout mice compared with the wild-type mice.

The above results show that administering the anti-DNAM-1 antibody to a living body may reduce renal fibrosis.

Test Example 16

(Study of Inflammatory Enteritis)

A study of inflammatory enteritis was conducted using DNAM-1 gene knockout mice instead of the administration of the anti-DNAM-1 antibody. Wild-type mice were used as a reference. A mouse model of dextran sulfate (DSS)-induced colitis was used in the test.

First, DNAM-1 knockout mice (n=5) and wild-type mice (n=5) were bred and habituated from 3 days before the initiation of the test. In this stage, plain water was given to the mice. After the initiation of the test, the mice were bred with a 2% DSS aqueous solution instead of water, and changes in the weights of the mice were measured. The mice were slaughtered on the ninth day after the initiation of the test. The large intestines were harvested from the mice, and the lengths thereof were measured.

Figure 22:
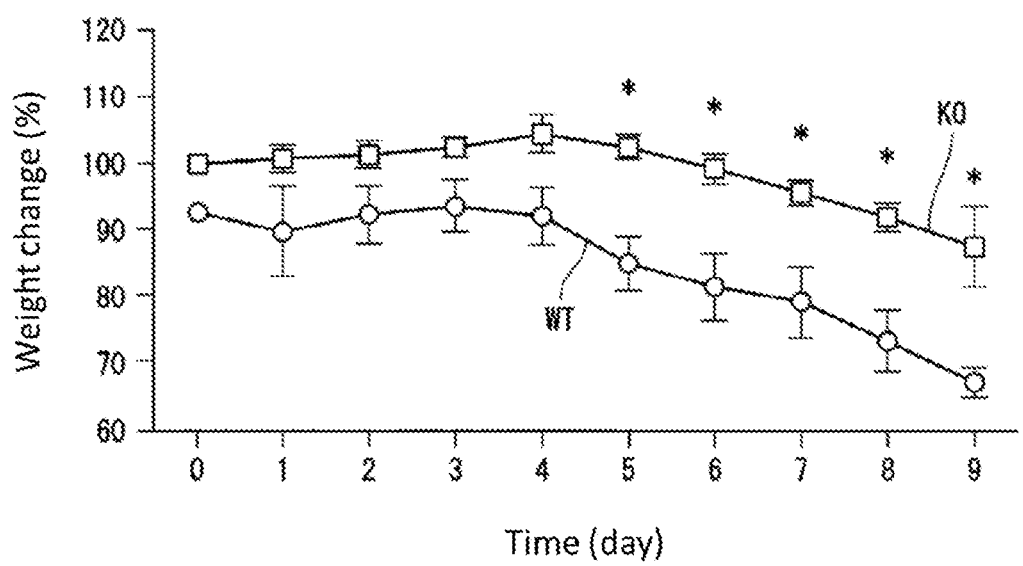
FIG. 22 is a graph illustrating the weights of control mice and DNAM-1 knockout mice used in Test example 16.

FIG. 22 is a graph illustrating the result of the weights of the control wild-type mice (WT) and the DNAM-1 knockout mice (KO) measured. In FIG. 22, the symbol "★" means that there was a significant difference therebetween with a significance level of less than 5%. The horizontal axis shows the time (day) elapsed from the initiation of the test. As a result, it was confirmed that a weight reduction resulting from inflammatory enteritis was significantly reduced in the DNAM-1 knockout mouse compared with the wild-type mouse.

Figure 23:
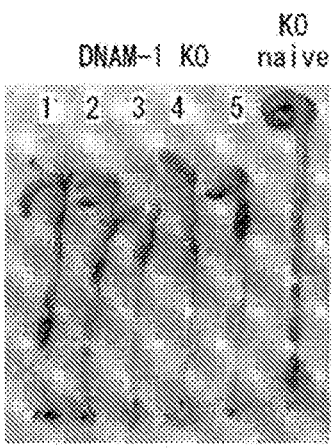
FIG. 23(a) is a photograph of the large intestine of a DNAM-1 knockout mouse which was harvested from the mouse on the ninth day from the initiation of the test in Test example 16.
FIG. 23(b) is a photograph of the large intestine of a control mouse which was harvested from the mouse on the ninth day from the initiation of the test in Test example 16.
FIG. 23(c) is a graph numerically representing the results shown in FIGS. 23(a) and 23(b).
Figure 23:
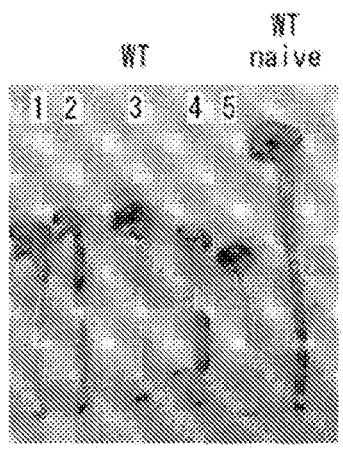
Figure 23:
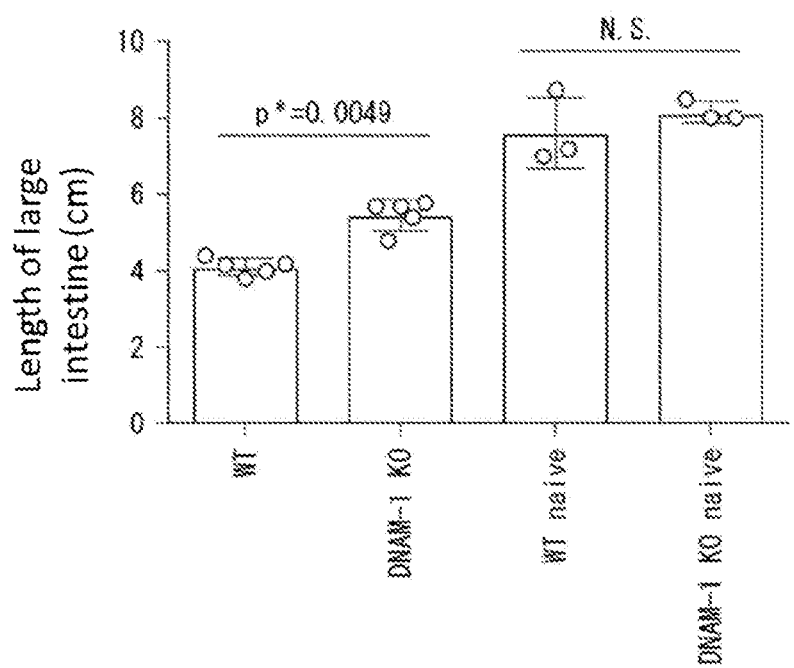

FIG. 23(a) is a photograph of the large intestines of the DNAM-1 knockout mice harvested on the ninth day from the initiation of the test. FIG. 23(b) is a photograph of the large intestines of the control wild-type mice harvested on the ninth day from the initiation of the test. FIG. 23(c) is a graph digitized the results shown in FIGS. 23(a) and 23(b). In FIGS. 23(a) to 23(c), "WT" denotes the results obtained by the test in which the wild-type mice were used, while "DNAM-1 KO" denotes the results obtained by the test in which the DNAM-1 knockout mice were used; and "naive" denotes the results obtained by the test in which water was given to a mouse instead of the 2% DSS aqueous solution. In FIG. 23(c), "N.S." means that there was no significant difference therebetween. As a result, it was confirmed that a reduction in the length of the intestine resulting from inflammatory enteritis was significantly reduced in the DNAM-1 knockout mice compared with the wild-type mice.

The above results show that administering the anti-DNAM-1 antibody to a living body may reduce the symptoms of inflammatory enteritis.

INDUSTRIAL APPLICABILITY

According to the present invention, a technology for reducing human immune responses may be provided.

---

The invention claimed is:

1. An anti-human DNAM-1 monoclonal antibody or a fragment thereof, comprising a heavy-chain variable region having the amino acid sequence of SEQ ID NO: 7 and a light-chain variable region having the amino acid sequence of SEQ ID NO: 8.

2. The anti-human DNAM-1 monoclonal antibody or a fragment thereof according to claim 1, the antibody or a fragment thereof being a humanized antibody or a fragment of a humanized type antibody.

* * * * *

SEQUENCE LISTING

```
<160> NUMBER OF SEQ ID NOS: 21

<210> SEQ ID NO 1
<211> LENGTH: 9
<212> TYPE: PRT
<213> ORGANISM: Mus musculus
<220> FEATURE:
<221> NAME/KEY: misc_feature
<223> OTHER INFORMATION: mAb No.1 heavy chain CDR1

<400> SEQUENCE: 1

Gly Tyr Ser Ile Thr Ser Gly Tyr Tyr
1               5

<210> SEQ ID NO 2
<211> LENGTH: 7
<212> TYPE: PRT
<213> ORGANISM: Mus musculus
<220> FEATURE:
<221> NAME/KEY: misc_feature
<223> OTHER INFORMATION: mAb No.1 heavy chain CDR2

<400> SEQUENCE: 2

Ile Ser Tyr Asp Gly Ser Asn
1               5

<210> SEQ ID NO 3
<211> LENGTH: 2
<212> TYPE: PRT
<213> ORGANISM: Mus musculus
<220> FEATURE:
<221> NAME/KEY: misc_feature
<223> OTHER INFORMATION: mAb No.1 heavy chain CDR3

<400> SEQUENCE: 3

Ala Arg
1
```

<210> SEQ ID NO 4
<211> LENGTH: 6
<212> TYPE: PRT
<213> ORGANISM: Mus musculus
<220> FEATURE:
<221> NAME/KEY: misc_feature
<223> OTHER INFORMATION: mAb No.1 light chain CDR1

<400> SEQUENCE: 4

Gln Ser Val Ser Asn Asp
1               5

<210> SEQ ID NO 5
<211> LENGTH: 3
<212> TYPE: PRT
<213> ORGANISM: Mus musculus
<220> FEATURE:
<221> NAME/KEY: misc_feature
<223> OTHER INFORMATION: mAb No.1 light chain CDR2

<400> SEQUENCE: 5

Tyr Ala Ser
1

<210> SEQ ID NO 6
<211> LENGTH: 7
<212> TYPE: PRT
<213> ORGANISM: Mus musculus
<220> FEATURE:
<221> NAME/KEY: misc_feature
<223> OTHER INFORMATION: mAb No.1 light chain CDR3

<400> SEQUENCE: 6

Gln Gln Asp Tyr Ser Ser Pro
1               5

<210> SEQ ID NO 7
<211> LENGTH: 122
<212> TYPE: PRT
<213> ORGANISM: Mus musculus
<220> FEATURE:
<221> NAME/KEY: misc_feature
<223> OTHER INFORMATION: mAb No.1 heavy chain variable region

<400> SEQUENCE: 7

Ser Gln Ser Leu Ser Leu Thr Cys Ser Val Thr Gly Tyr Ser Ile Thr
1               5                   10                  15

Ser Gly Tyr Tyr Trp Asn Trp Ile Arg Gln Phe Pro Gly Asn Lys Leu
            20                  25                  30

Glu Trp Met Gly Tyr Ile Ser Tyr Asp Gly Ser Asn Asn Tyr Asn Pro
        35                  40                  45

Ser Leu Lys Asn Arg Ile Ser Ile Thr Arg Asp Thr Ser Lys Asn Gln
    50                  55                  60

Phe Phe Leu Lys Leu Asn Ser Val Thr Thr Glu Asp Thr Ala Thr Tyr
65                  70                  75                  80

Tyr Cys Ala Arg Ala Tyr Tyr Gly Asn Tyr Val Gly Tyr Phe Asp Val
                85                  90                  95

Trp Gly Ala Gly Thr Thr Val Thr Val Ser Ser Ala Lys Thr Thr Pro
            100                 105                 110

Pro Ser Val Tyr Pro Leu Ala Pro Gly Lys
            115                 120

<210> SEQ ID NO 8
<211> LENGTH: 108

```
<212> TYPE: PRT
<213> ORGANISM: Mus musculus
<220> FEATURE:
<221> NAME/KEY: misc_feature
<223> OTHER INFORMATION: mAb No.1 light chain variable region

<400> SEQUENCE: 8
```

Arg Val Thr Ile Thr Cys Lys Ala Ser Gln Ser Val Ser Asn Asp Val
1               5                   10                  15

Ala Trp Tyr Gln Gln Lys Pro Gly Gln Ser Pro Lys Leu Leu Ile Tyr
            20                  25                  30

Tyr Ala Ser Asn Arg Tyr Thr Gly Val Pro Asp Arg Phe Thr Gly Ser
        35                  40                  45

Gly Tyr Gly Thr Asp Phe Thr Phe Thr Ile Ser Thr Val Gln Ala Glu
    50                  55                  60

Asp Leu Ala Val Tyr Phe Cys Gln Gln Asp Tyr Ser Ser Pro Leu Thr
65                  70                  75                  80

Phe Gly Ala Gly Thr Lys Leu Glu Leu Lys Arg Ala Asp Ala Ala Pro
                85                  90                  95

Thr Val Ser Ile Phe Pro Pro Ser Ser Glu Gln Thr
            100                 105

```
<210> SEQ ID NO 9
<211> LENGTH: 126
<212> TYPE: PRT
<213> ORGANISM: Mus musculus
<220> FEATURE:
<221> NAME/KEY: misc_feature
<223> OTHER INFORMATION: mAb No.2 heavy chain variable region

<400> SEQUENCE: 9
```

Ser Gln Ser Leu Ser Leu Thr Cys Thr Val Thr Gly Tyr Ser Ile Thr
1               5                   10                  15

Ser Asp Tyr Ala Trp Asn Trp Ile Arg Gln Phe Pro Gly Asn Lys Leu
            20                  25                  30

Glu Trp Met Gly Tyr Ile Ser Tyr Ser Gly Thr Thr Thr Tyr Asn Pro
        35                  40                  45

Ser Leu Lys Ser Arg Ile Ser Ile Thr Arg Asp Thr Ser Lys Asn Gln
    50                  55                  60

Phe Phe Leu Gln Leu Asn Ser Val Thr Thr Glu Asp Thr Ala Thr Tyr
65                  70                  75                  80

Tyr Cys Ala Glu Leu Ser Met Asp Tyr Trp Gly Gln Gly Thr Ser Val
                85                  90                  95

Thr Val Ser Ser Ala Lys Thr Thr Pro Pro Ser Val Tyr Pro Leu Ala
            100                 105                 110

Pro Gly Asn Leu Asn Ser Ser Thr Ser Phe Ser Ser Leu Gly
        115                 120                 125

```
<210> SEQ ID NO 10
<211> LENGTH: 150
<212> TYPE: PRT
<213> ORGANISM: Mus musculus
<220> FEATURE:
<221> NAME/KEY: misc_feature
<223> OTHER INFORMATION: mAb No.2 light chain variable region

<400> SEQUENCE: 10
```

Asp Ile Val Leu Ser Gln Ser Pro Ala Ile Leu Ser Val Ser Pro Gly
1               5                   10                  15

Glu Arg Val Ser Phe Ser Cys Arg Ala Ser Gln Ser Ile Gly Thr Ser

```
                20                  25                  30

Ile His Trp Tyr Gln Gln Arg Thr Asn Gly Ser Pro Arg Leu Leu Ile
            35                  40                  45

Lys Tyr Ala Ser Glu Ser Ile Ser Gly Ile Pro Ser Arg Phe Ser Gly
        50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Ser Arg Ser Trp Pro Leu
                85                  90                  95

Thr Phe Gly Ala Gly Thr Lys Leu Glu Leu Lys Arg Ala Asp Ala Ala
            100                 105                 110

Pro Thr Val Ser Ile Phe Pro Pro Ser Ser Glu Gln Asn His Glu Phe
        115                 120                 125

Trp Ile Arg Tyr Val Thr Arg Leu Gln His Ala Trp Tyr Arg Ala Phe
    130                 135                 140

Pro Ile Gly Val Asp Glu
145                 150

<210> SEQ ID NO 11
<211> LENGTH: 115
<212> TYPE: PRT
<213> ORGANISM: Mus musculus
<220> FEATURE:
<221> NAME/KEY: misc_feature
<223> OTHER INFORMATION: mAb No.3 heavy chain variable region

<400> SEQUENCE: 11

Glu Ile Ser Cys Lys Ala Ser Gly Tyr Thr Phe Thr Asn Tyr Trp Leu
1               5                   10                  15

Gly Trp Val Lys Gln Arg Pro Gly His Gly Leu Glu Trp Ile Gly Asp
            20                  25                  30

Ile Tyr Pro Gly Gly Gly Tyr Thr Asn Tyr Asn Glu Lys Phe Lys Gly
        35                  40                  45

Lys Ala Thr Leu Thr Ala Asp Thr Ser Ser Ser Thr Ala Tyr Met Gln
    50                  55                  60

Leu Ser Ser Leu Thr Ser Glu Asp Ser Ala Val Tyr Phe Cys Ala Asn
65                  70                  75                  80

Ala Tyr Tyr Arg Tyr Lys Gly Phe Ala Tyr Trp Gly Gln Gly Thr Leu
                85                  90                  95

Val Thr Val Ser Ala Ala Lys Thr Thr Ala Pro Ser Val Tyr Pro Leu
            100                 105                 110

Ala Pro Leu
        115

<210> SEQ ID NO 12
<211> LENGTH: 112
<212> TYPE: PRT
<213> ORGANISM: Mus musculus
<220> FEATURE:
<221> NAME/KEY: misc_feature
<223> OTHER INFORMATION: mAb No.3 light chain variable region

<400> SEQUENCE: 12

Val Thr Met Ser Cys Lys Ser Ser Gln Ser Leu Leu Tyr Ser Ser Asn
1               5                   10                  15

Gln Lys Asn Tyr Leu Ala Trp Tyr Gln Gln Lys Pro Gly Gln Ala Pro
            20                  25                  30

Lys Leu Leu Ile Tyr Trp Ala Ser Thr Arg Glu Ser Gly Val Pro Asp
```

```
                    35                  40                  45

Arg Phe Thr Gly Ser Gly Ser Gly Thr Asp Phe Thr Leu Thr Ile Ser
 50                  55                  60

Ser Val Lys Ala Glu Asp Leu Ala Val Tyr Tyr Cys Gln Gln Tyr Tyr
 65                  70                  75                  80

Ser Tyr Pro Trp Thr Phe Gly Gly Gly Thr Lys Leu Glu Ile Lys Arg
                 85                  90                  95

Ala Asp Ala Ala Pro Thr Val Ser Ile Phe Pro Pro Ser Ser Glu Gln
            100                 105                 110

<210> SEQ ID NO 13
<211> LENGTH: 117
<212> TYPE: PRT
<213> ORGANISM: Mus musculus
<220> FEATURE:
<221> NAME/KEY: misc_feature
<223> OTHER INFORMATION: mAb No.4 heavy chain variable region

<400> SEQUENCE: 13

Lys Trp Gly Leu Ser Glu Ile Ser Cys Lys Ala Ser Gly Tyr Thr Phe
 1                   5                  10                  15

Thr Asp Tyr Asn Met His Trp Val Lys Gln Ser His Gly Lys Ser Leu
                 20                  25                  30

Glu Trp Ile Gly Tyr Ile Tyr Pro Tyr Asn Gly Gly Thr Gly Tyr Asn
            35                  40                  45

Gln Lys Phe Lys Ser Lys Ala Thr Leu Thr Val Asp Asn Ser Ser Ser
 50                  55                  60

Thr Ala Tyr Met Glu Leu Arg Ser Leu Thr Ser Glu Asp Ser Ala Val
 65                  70                  75                  80

Tyr Tyr Cys Ala Gly Tyr Trp Tyr Phe Asp Val Trp Gly Ala Gly Thr
                 85                  90                  95

Thr Val Thr Val Ser Ser Ala Lys Thr Thr Pro Pro Ser Val Tyr Pro
            100                 105                 110

Leu Ala Pro Trp Lys
        115

<210> SEQ ID NO 14
<211> LENGTH: 109
<212> TYPE: PRT
<213> ORGANISM: Mus musculus
<220> FEATURE:
<221> NAME/KEY: misc_feature
<223> OTHER INFORMATION: mAb No.4 light chain variable region

<400> SEQUENCE: 14

Glu Lys Val Ser Ile Thr Cys Lys Ala Ser Gln Asp Val Gly Thr Ala
 1                   5                  10                  15

Val Ala Trp Tyr Gln Gln Lys Pro Gly Gln Ser Pro Lys Leu Leu Ile
                 20                  25                  30

Tyr Trp Ala Ser Thr Arg His Thr Gly Val Pro Asp Arg Phe Thr Gly
            35                  40                  45

Ser Gly Ser Gly Thr Asp Phe Thr Leu Thr Ile Ser Asn Val Gln Ser
 50                  55                  60

Glu Asp Leu Ala Asp Tyr Phe Cys Gln Gln Tyr Ser Ser Tyr Pro Trp
 65                  70                  75                  80

Thr Phe Gly Gly Gly Thr Lys Leu Glu Ile Lys Arg Ala Asp Ala Ala
                 85                  90                  95

Pro Thr Val Ser Ile Phe Pro Pro Ser Ser Glu Gln Arg
```

<210> SEQ ID NO 15
<211> LENGTH: 113
<212> TYPE: PRT
<213> ORGANISM: Mus musculus
<220> FEATURE:
<221> NAME/KEY: misc_feature
<223> OTHER INFORMATION: mAb No.5 heavy chain variable region

<400> SEQUENCE: 15

Ser Val Thr Gly Tyr Ser Ile Thr Ser Gly Tyr Tyr Trp Asn Trp Ile
1               5                   10                  15

Arg Gln Phe Pro Gly Asn Lys Leu Glu Trp Met Gly Tyr Ile Ser Tyr
            20                  25                  30

Asp Gly Ser Asn Asn Tyr Asn Pro Ser Leu Lys Asn Arg Ile Ser Ile
        35                  40                  45

Thr Arg Asp Thr Ser Lys Asn Gln Phe Phe Leu Lys Leu Asn Ser Val
    50                  55                  60

Thr Thr Glu Asp Thr Ala Thr Tyr Tyr Cys Ala Arg Glu Arg Val Met
65                  70                  75                  80

Ile Thr Ala Ser Phe Asp Tyr Trp Gly Gln Gly Thr Thr Leu Thr Val
                85                  90                  95

Ser Ser Ala Lys Thr Thr Pro Pro Ser Val Tyr Pro Leu Ala Pro Gly
            100                 105                 110

Lys

<210> SEQ ID NO 16
<211> LENGTH: 112
<212> TYPE: PRT
<213> ORGANISM: Mus musculus
<220> FEATURE:
<221> NAME/KEY: misc_feature
<223> OTHER INFORMATION: mAb No.5 light chain variable region

<400> SEQUENCE: 16

Ser Ala Leu Trp Glu Arg Val Ser Leu Thr Cys Arg Ala Ser Gln Glu
1               5                   10                  15

Ile Ser Gly Tyr Leu Ser Trp Leu Gln Gln Lys Pro Asp Gly Thr Ile
            20                  25                  30

Lys Arg Leu Ile Tyr Ala Ala Ser Thr Leu Asp Ser Gly Val Pro Lys
        35                  40                  45

Arg Phe Ser Gly Ser Arg Ser Gly Ser Asp Tyr Ser Leu Thr Ile Ser
    50                  55                  60

Ser Leu Glu Ser Glu Asp Phe Ala Asp Tyr Tyr Cys Leu Gln Tyr Ala
65                  70                  75                  80

Ser Tyr Pro Trp Thr Phe Gly Gly Gly Thr Lys Leu Glu Ile Lys Arg
                85                  90                  95

Ala Asp Ala Ala Pro Thr Val Ser Ile Phe Pro Pro Ser Ser Glu Gln
            100                 105                 110

<210> SEQ ID NO 17
<211> LENGTH: 121
<212> TYPE: PRT
<213> ORGANISM: Mus musculus
<220> FEATURE:
<221> NAME/KEY: misc_feature
<223> OTHER INFORMATION: mAb No.6 heavy chain variable region

<400> SEQUENCE: 17

```
Ser Gln Ser Leu Ser Leu Thr Cys Ser Val Thr Gly Tyr Ser Ile Thr
1               5                   10                  15

Ser Gly Tyr Tyr Trp Asn Trp Ile Arg Gln Phe Pro Gly Asn Lys Leu
            20                  25                  30

Glu Trp Met Gly Tyr Ile Ser Tyr Asp Gly Ser Asn Asn Tyr Asn Pro
                35                  40                  45

Ser Leu Lys Asn Arg Ile Ser Ile Thr Arg Asp Thr Ser Lys Asn Gln
        50                  55                  60

Phe Phe Leu Lys Leu Asn Ser Val Thr Thr Glu Asp Thr Ala Thr Tyr
65                  70                  75                  80

Tyr Cys Ala Arg Glu Arg Val Met Ile Thr Ala Ser Phe Asp Tyr Trp
                85                  90                  95

Gly Gln Gly Thr Thr Leu Thr Val Ser Ser Ala Lys Thr Thr Pro Pro
                100                 105                 110

Ser Val Tyr Pro Leu Ala Pro Gly Lys
        115                 120
```

```
<210> SEQ ID NO 18
<211> LENGTH: 97
<212> TYPE: PRT
<213> ORGANISM: Mus musculus
<220> FEATURE:
<221> NAME/KEY: misc_feature
<223> OTHER INFORMATION: mAb No.6 light chain variable region

<400> SEQUENCE: 18

Arg Ala Ser Gly Asn Ile His Asn Tyr Leu Ala Trp Tyr Gln Gln Lys
1               5                   10                  15

Gln Gly Lys Ser Pro Gln Leu Leu Val Tyr Asn Ala Lys Thr Leu Ala
            20                  25                  30

Asp Gly Val Pro Ser Arg Phe Ser Gly Ser Gly Ser Gly Thr Gln Tyr
                35                  40                  45

Ser Leu Lys Ile Asn Ser Leu Gln Pro Glu Asp Phe Gly Ser Tyr Tyr
        50                  55                  60

Cys Gln His Phe Trp Ser Thr Pro Tyr Thr Phe Gly Gly Gly Thr Lys
65                  70                  75                  80

Leu Glu Ile Lys Arg Ala Asp Ala Ala Pro Thr Val Ser Ile Phe Pro
                85                  90                  95

Pro
```

```
<210> SEQ ID NO 19
<211> LENGTH: 379
<212> TYPE: DNA
<213> ORGANISM: Mus musculus
<220> FEATURE:
<221> NAME/KEY: misc_feature
<223> OTHER INFORMATION: mAb No.1 heavy chain variable region

<400> SEQUENCE: 19
cagccgctac ttctcagtct ctgtctctca cctgctctgt cactggctac tccatcacca      60
gtggttatta ctggaactgg atccggcagt ttccaggaaa caaactggaa tggatgggct     120
acataagcta cgacggtagc aataactaca cccatctctc aaaaatcga atctccatca     180 ctcgtgacac atctaagaac cagttttttcc tgaagttgaa ttctgtgact actgaggaca     240
cagctacata ttactgtgca agggcctact atggtaacta cgtggggtac ttcgatgtct     300
ggggcgcagg gaccacggtc accgtctcct cagccaaaac gacacccca tcggtctatc     360 cactggcccc tggaaaaaa                                                  379
```

```
<210> SEQ ID NO 20
<211> LENGTH: 339
<212> TYPE: DNA
<213> ORGANISM: Mus musculus
<220> FEATURE:
<221> NAME/KEY: misc_feature
<223> OTHER INFORMATION: mAb No.1 light chain variable region

<400> SEQUENCE: 20
gttcagcagg agacagggtt accataacct gcaaggccag tcagagtgtg agtaatgatg      60
tagcttggta ccaacagaag ccagggcagt ctcctaaact gctgatatac tatgcatcca     120
atcgctacac tggagtccct gatcgcttca ctggcagtgg atatgggacg gatttcactt     180
tcaccatcag cactgtgcag gctgaagacc tggcagttta tttctgtcag caggattata     240
gctctccgct cacgttcggt gctgggacca agctggagct gaaacgggct gatgctgcac     300
caactgtatc catcttccca ccatccagtg agcagagag                            339

<210> SEQ ID NO 21
<211> LENGTH: 15
<212> TYPE: PRT
<213> ORGANISM: Artificial Sequence
<220> FEATURE:
<223> OTHER INFORMATION: scFv linker

<400> SEQUENCE: 21

Gly Gly Gly Gly Ser Gly Gly Gly Gly Ser Gly Gly Gly Gly Ser
1               5                   10                  15
```